US008945535B2

(12) United States Patent
Steinwachs et al.

(10) Patent No.: US 8,945,535 B2
(45) Date of Patent: Feb. 3, 2015

(54) IMPLANT FOR THE REPAIR OF A CARTILAGE DEFECT AND METHOD FOR MANUFACTURING THE IMPLANT

(75) Inventors: Matthias R. Steinwachs, Zunikon (CH); Peter Bittmann, Zurich (CH)

(73) Assignee: Zimmer Orthobiologics, Inc., Austin, TX (US)

( * ) Notice: Subject to any disclaimer, the term of this patent is extended or adjusted under 35 U.S.C. 154(b) by 326 days.

(21) Appl. No.: 11/997,769

(22) PCT Filed: Sep. 18, 2006

(86) PCT No.: PCT/CH2006/000503
§ 371 (c)(1),
(2), (4) Date: Jun. 27, 2008

(87) PCT Pub. No.: WO2007/033509
PCT Pub. Date: Mar. 29, 2007

(65) Prior Publication Data
US 2008/0269895 A1    Oct. 30, 2008

(30) Foreign Application Priority Data
Sep. 20, 2005  (EP) .................................. 05405547

(51) Int. Cl.
| *A01N 63/02* | (2006.01) |
| *A61K 9/00* | (2006.01) |
| *A61F 2/08* | (2006.01) |
| *C12N 5/071* | (2010.01) |
| *A61L 27/38* | (2006.01) |
| *A61L 27/36* | (2006.01) |

(52) U.S. Cl.
CPC ......... *A61L 27/3817* (2013.01); *A61L 27/3612* (2013.01); *A61L 27/3852* (2013.01)
USPC ....... 424/93.7; 424/423; 424/484; 623/13.17; 435/395; 514/17.2

(58) Field of Classification Search
CPC ..... A61K 9/0024; A61F 2/30756; A61F 2/28; A61F 2/38; A61F 2002/30062; A61F 2002/30764; A61F 2002/30766; A61F 2002/30535; A61L 27/3817; A61L 27/3683; A61L 27/3633
USPC .............. 424/93.7, 423, 484, 548; 623/13.17; 435/395; 514/17.2
See application file for complete search history.

(56) References Cited

U.S. PATENT DOCUMENTS

| 4,356,261 A | 10/1982 | Kuettner ......................... 435/68 |
| 4,394,370 A | 7/1983 | Jefferies |
| 4,516,276 A | 5/1985 | Mittelmeier |
| 4,609,551 A | 9/1986 | Caplan et al. |
| 4,624,672 A | 11/1986 | Lenkauskas .................... 623/10 |
| 4,627,853 A | 12/1986 | Campbell et al. ............... 623/16 |
| 4,846,835 A | 7/1989 | Grande ........................... 623/11 |
| 5,007,934 A | 4/1991 | Stone |
| 5,206,023 A | 4/1993 | Hunziker ...................... 424/423 |
| 5,326,357 A | 7/1994 | Kandel ............................ 623/16 |
| 5,368,858 A | 11/1994 | Hunziker ...................... 424/423 |
| 5,578,492 A | 11/1996 | Fedun |
| 5,629,009 A | 5/1997 | Laurencin et al. |
| 5,707,962 A | 1/1998 | Chen et al. |
| 5,713,374 A | 2/1998 | Pachence et al. |
| 5,741,685 A | 4/1998 | Vacanti |
| 5,749,874 A | 5/1998 | Schwartz ........................ 606/75 |
| 5,837,235 A | 11/1998 | Mueller et al. ............... 424/93.7 |
| 5,842,477 A | 12/1998 | Naughton et al. ............ 128/898 |
| 5,902,741 A | 5/1999 | Purchio et al. ........... 435/240.23 |
| 5,908,784 A | 6/1999 | Johnstone et al. ............ 435/372 |
| 5,928,945 A | 7/1999 | Seliktar et al. |
| 5,993,844 A | 11/1999 | Abraham et al. ............. 424/423 |
| 6,017,348 A | 1/2000 | Hart et al. ...................... 606/79 |
| 6,060,306 A | 5/2000 | Flatt et al. ................... 435/297.2 |
| 6,080,194 A | 6/2000 | Pachence et al. |
| 6,107,085 A | 8/2000 | Coughlin et al. |
| 6,150,163 A | 11/2000 | McPherson et al. |
| 6,171,340 B1 * | 1/2001 | McDowell ................. 623/18.11 |
| 6,179,871 B1 | 1/2001 | Halpern ..................... 623/11.11 |
| 6,183,737 B1 | 2/2001 | Zaleske et al. |
| 6,197,061 B1 | 3/2001 | Masuda et al. ............. 623/11.11 |
| 6,235,316 B1 | 5/2001 | Adkisson ..................... 424/548 |

(Continued)

FOREIGN PATENT DOCUMENTS

| AU | 742613 | 10/1998 |
| AU | 7100398 | 10/1998 |

(Continued)

OTHER PUBLICATIONS

Takigawa et al. Bone Miner. vol. 6. (p. 1), 1987 Abstract Only.*

(Continued)

*Primary Examiner* — Anne Marie S Wehbe
(74) *Attorney, Agent, or Firm* — Schwegman Lundberg & Woessner, P.A.

(57) ABSTRACT

For the repair of a cartilage defect in a human or animal patient use is made of an implant comprising an implant body including a natural cartilage matrix and being coated with cells having a chondrogenic potential. These cells are produced by in vitro cell proliferation starting from chondrocytes isolated from a cartilage biopsy. The chondrocytes which are de-differentiated during cell proliferation are re-differentiated during tissue culturing and are in particular suitable for producing and maintaining the cartilage matrix of the implant body. The cells adhering to the surface of the implant body are preferably also chondrocytes being de-differentiated by cell proliferation, but not re-differentiated, and are therefore particularly suitable for integrating the implant in the defect. Due to the cells adhering to the surface of the implant body, the implant is successfully integrated in the viable tissue surrounding the defect.

21 Claims, 5 Drawing Sheets

(56) References Cited

U.S. PATENT DOCUMENTS

| | | | |
|---|---|---|---|
| 6,242,247 B1 | 6/2001 | Rieser et al. | 435/297.1 |
| 6,251,143 B1 | 6/2001 | Schwartz et al. | 623/23.72 |
| 6,387,693 B2 | 5/2002 | Rieser et al. | |
| 6,451,060 B2 | 9/2002 | Masuda et al. | 623/23.72 |
| 6,454,811 B1 | 9/2002 | Sherwood et al. | |
| 6,492,163 B1 | 12/2002 | Yoo et al. | |
| 6,497,903 B1 | 12/2002 | Hennink et al. | |
| 6,569,172 B2 | 5/2003 | Asculai et al. | 606/151 |
| 6,582,471 B1 | 6/2003 | Bittmann et al. | 623/23.63 |
| 6,582,960 B1 | 6/2003 | Martin et al. | |
| 6,623,963 B1 | 9/2003 | Müller et al. | 435/395 |
| 6,662,805 B2 | 12/2003 | Frondoza et al. | |
| 6,852,125 B2 | 2/2005 | Simon et al. | 623/16.11 |
| 6,911,202 B2 | 6/2005 | Amir et al. | 424/93.7 |
| 6,911,496 B2 | 6/2005 | Rhee et al. | |
| 7,087,227 B2 | 8/2006 | Adkisson | |
| RE41,286 E | 4/2010 | Atkinson et al. | |
| 7,879,604 B2 | 2/2011 | Seyedin et al. | |
| 8,025,901 B2 | 9/2011 | Kao et al. | |
| 8,137,689 B1 | 3/2012 | Grogan et al. | |
| 8,173,162 B2 | 5/2012 | Vilei et al. | |
| 2001/0006634 A1 | 7/2001 | Zaleske et al. | 424/93.7 |
| 2001/0010023 A1 | 7/2001 | Schwartz et al. | 623/23.72 |
| 2001/0012965 A1 | 8/2001 | Masuda et al. | 623/11.11 |
| 2001/0014473 A1 | 8/2001 | Rieser | |
| 2001/0039455 A1 | 11/2001 | Simon et al. | 623/23.51 |
| 2002/0009805 A1* | 1/2002 | Nevo et al. | 435/366 |
| 2002/0052044 A1 | 5/2002 | Jeschke et al. | 435/325 |
| 2002/0072533 A1 | 6/2002 | Schrier et al. | 514/364 |
| 2002/0082623 A1 | 6/2002 | Osther et al. | |
| 2002/0110544 A1 | 8/2002 | Goldberg et al. | 424/93.7 |
| 2003/0077821 A1 | 4/2003 | Sah et al. | 435/366 |
| 2003/0100947 A1 | 5/2003 | Nadler et al. | 623/11.11 |
| 2003/0134792 A1 | 7/2003 | Pike et al. | 514/12 |
| 2003/0153078 A1 | 8/2003 | Libera et al. | |
| 2003/0211992 A1 | 11/2003 | Chen et al. | 514/12 |
| 2004/0030404 A1 | 2/2004 | Noll et al. | |
| 2004/0030406 A1* | 2/2004 | Ochi et al. | 623/23.72 |
| 2004/0033212 A1 | 2/2004 | Thomson et al. | |
| 2004/0039447 A1 | 2/2004 | Simon et al. | 623/13.11 |
| 2004/0097405 A1 | 5/2004 | Schrier et al. | 514/2 |
| 2004/0162622 A1 | 8/2004 | Simon et al. | 623/23.5 |
| 2004/0181232 A1 | 9/2004 | Re et al. | 606/86 |
| 2004/0219182 A1 | 11/2004 | Gomes et al. | 424/423 |
| 2005/0124038 A1 | 6/2005 | Aguiar et al. | |
| 2005/0152882 A1 | 7/2005 | Kizer et al. | |
| 2005/0196387 A1 | 9/2005 | Seyedin et al. | |
| 2005/0226856 A1 | 10/2005 | Ahlfors | 424/93.7 |
| 2005/0244363 A1 | 11/2005 | Hossainy et al. | |
| 2005/0244454 A1 | 11/2005 | Elson et al. | |
| 2005/0265980 A1 | 12/2005 | Chen et al. | |
| 2006/0008530 A1 | 1/2006 | Seyedin et al. | |
| 2006/0024373 A1 | 2/2006 | Shahar et al. | |
| 2006/0073588 A1 | 4/2006 | Adkisson et al. | |
| 2006/0099706 A1 | 5/2006 | Massey et al. | |
| 2006/0251631 A1 | 11/2006 | Adkisson, IV et al. | |
| 2006/0275273 A1 | 12/2006 | Seyedin et al. | |
| 2006/0281173 A1 | 12/2006 | Fukuda et al. | |
| 2007/0077236 A1 | 4/2007 | Osther | |
| 2007/0087032 A1 | 4/2007 | Chang et al. | |
| 2007/0118218 A1 | 5/2007 | Hooper | |
| 2007/0128155 A1 | 6/2007 | Seyedin et al. | |
| 2007/0148242 A1 | 6/2007 | Vilei et al. | 424/484 |
| 2007/0212389 A1 | 9/2007 | Weiss et al. | |
| 2007/0233259 A1 | 10/2007 | Muhanna | |
| 2008/0039939 A1 | 2/2008 | Iwamoto | |
| 2008/0081369 A1 | 4/2008 | Adkisson, IV et al. | |
| 2008/0095736 A1 | 4/2008 | Pathak et al. | |
| 2008/0199429 A1 | 8/2008 | Hollander et al. | |
| 2008/0299214 A1 | 12/2008 | Seyedin et al. | |
| 2009/0143867 A1 | 6/2009 | Gage et al. | |
| 2011/0256095 A1 | 10/2011 | Seyedin et al. | |
| 2012/0009224 A1 | 1/2012 | Kizer et al. | |
| 2012/0263683 A1 | 10/2012 | Vilei et al. | |

FOREIGN PATENT DOCUMENTS

| | | | |
|---|---|---|---|
| AU | 766593 | 8/2000 | |
| AU | 2006282754 | 3/2007 | |
| CA | 2285382 | 10/1998 | |
| DE | 4306661 A1 | 9/1994 | |
| EP | 0 396 138 A2 | 11/1990 | |
| EP | 0 339 607 B1 | 2/1993 | |
| EP | 1 099 443 A1 | 5/2001 | |
| EP | 1270025 A2 | 6/2002 | |
| EP | 0 896 825 B1 | 7/2002 | |
| EP | 1270025 A3 | 3/2003 | |
| EP | 0747066 B1 | 12/2003 | |
| EP | 1 464 697 A1 | 10/2004 | |
| EP | 0 656 767 B1 | 2/2005 | |
| EP | 0 868 505 B1 | 2/2005 | |
| EP | 1 112 348 B1 | 11/2005 | |
| EP | 1 632 563 A1 | 3/2006 | |
| EP | 1 788 077 | 5/2007 | |
| EP | 1691727 B1 | 7/2011 | |
| EP | 1753860 B1 | 4/2012 | |
| JP | 1265968 A | 10/1989 | |
| JP | 2156954 A | 6/1990 | |
| JP | 4505717 A | 10/1992 | |
| JP | 5501208 A | 3/1993 | |
| JP | 5505404 A | 8/1993 | |
| JP | 6505258 A | 6/1994 | |
| JP | 6507173 A | 8/1994 | |
| JP | 9505305 A | 5/1997 | |
| JP | 11506615 A | 6/1999 | |
| JP | 2000513214 A | 10/2000 | |
| JP | 2001519700 T | 10/2001 | |
| JP | 2002502226 A | 1/2002 | |
| JP | 2002233567 A | 8/2002 | |
| JP | 2003505143 A | 2/2003 | |
| JP | 2003534792 A | 5/2008 | |
| JP | 2008514254 A | 5/2008 | |
| WO | WO-9012603 A1 | 11/1990 | |
| WO | WO-9209697 A1 | 6/1992 | |
| WO | WO-9319168 A1 | 9/1993 | |
| WO | WO-9420151 A1 | 9/1994 | |
| WO | WO95/30383 A1 | 11/1995 | |
| WO | WO95/33821 A1 | 12/1995 | |
| WO | WO-9634955 A1 | 11/1996 | |
| WO | WO 96/39170 | 12/1996 | |
| WO | WO-9639170 A1 | 12/1996 | |
| WO | WO97/30662 A1 | 8/1997 | |
| WO | WO-9738676 A1 | 10/1997 | |
| WO | WO-97/46665 A1 | 12/1997 | |
| WO | WO 98/04681 | 2/1998 | |
| WO | WO-9822492 A1 | 5/1998 | |
| WO | WO 98/44874 | 10/1998 | |
| WO | WO98/55594 A2 | 12/1998 | |
| WO | WO-9908728 A1 | 2/1999 | |
| WO | WO-9915637 A1 | 4/1999 | |
| WO | WO00/17321 A3 | 3/2000 | |
| WO | WO00/51527 A1 | 9/2000 | |
| WO | WO-0106949 A2 | 2/2001 | |
| WO | WO-0117463 A1 | 3/2001 | |
| WO | WO 01/34166 * | 5/2001 | A61K 35/32 |
| WO | WO01/34166 | 5/2001 | |
| WO | WO01/35968 A1 | 5/2001 | |
| WO | WO 01/68811 | 9/2001 | |
| WO | WO-0192473 A2 | 12/2001 | |
| WO | WO02/10348 A2 | 2/2002 | |
| WO | WO-02070030 A1 | 9/2002 | |
| WO | WO03/024463 A1 | 3/2003 | |
| WO | WO03/064598 A2 | 8/2003 | |
| WO | WO 03/100417 | 12/2003 | |
| WO | WO2004/075940 | 9/2004 | |
| WO | WO 2004/078955 | 9/2004 | |
| WO | WO2004/083415 A1 | 9/2004 | |
| WO | WO-2004075940 A1 | 9/2004 | |
| WO | WO2004/104188 A1 | 12/2004 | |
| WO | WO 2004/110512 | 12/2004 | |
| WO | WO-2005011765 A1 | 2/2005 | |
| WO | WO 2005/058207 | 6/2005 | |
| WO | WO 2005/081870 | 9/2005 | |
| WO | WO2005/110278 A2 | 11/2005 | |

(56) References Cited

FOREIGN PATENT DOCUMENTS

| WO | WO 2006/017176 | 2/2006 |
|---|---|---|
| WO | WO-2006032915 A2 | 3/2006 |
| WO | WO 2006/039484 | 4/2006 |
| WO | WO 2006/121612 | 11/2006 |
| WO | WO 2007/025290 | 3/2007 |
| WO | WO-2007033509 A1 | 3/2007 |
| WO | WO 2007/067637 | 6/2007 |
| WO | WO-2007143726 A2 | 12/2007 |

OTHER PUBLICATIONS

Adolphe et al., *Biological Regulation of Chrondrocytes*, Chapter 4, pp. 105-139 (1992).
Atkinson et al., *Journal of Cellular Biochemistry* 65:325-339 (1997).
Atkinson et al., "Elucidation of Homeoprotein Cart-1 Function During In Vitro Chondrogenesis of C3H10T1/2 Micromass Cultures," *Annals New York Academy of Sciences*, 785:206-208 (1996).
Benz et al., *Biochemical and Biophysical Research Communications* 293:284-292 (2002).
Binette et al., *Journal of Orthopaedic Research* 16:207-216 (1998).
Bradham et al., *Clinical Orthopaedics and Related Research* 352:239-249 (1998).
Schulze-Tanzil et al., *Cell Tissue Res.* 308:371-379 (2002).
Trippel, *The Journal of Rheumatology* 22:129-132 (1995).
Akens, M.K., et al., In Vitro Studies of a Photo-oxidized Bovine Articular Cartilage, Journal of Veterinary Medicine, 2002, pp. 39-45, vol. 49, Blackwell Wissenschafts-Verlag, Berlin.
Alfredson, Hakan, et al., Superior results with continuous passive motion compared to active motion after periosteal transplantation, 1999, pp. 232-238, vol. 7, Knee Surg sports Trautnatol Arthrosc, Springer-Verlag, Germany.
Aston, Jayne E., et al., Repair of Articular Surfaces by Allografts of Articular and Growth-Plate Cartilage, 1986, pp. 29-35, vol. 68-B, No. 1, British Editorial Society of Bone and Joint Surgery, England.
Augenstein, D.C., et al., Effect of Shear on the Death of Two Strains of Mammalian Tissue Cells, 1971, pp. 409-418, vol. XIII, Biotechnology and Bioengineering, USA.
Aulthouse, Amy Lynn, et al., Expression of the Human Chondrocyte Phenotype in Vitro, 1989, pp. 659-668, vol. 25, No. 7, In Vitro Cellular & Developmental Biology, USA.
Bacsich, P., et al., The Significance of the Mucoprotein Content on the Survival of Homografts of Cartilage and Cornea, 1946, pp. 321-327, vol. LXII, Part III, P.R.S.E., USA.
Bartlett, W., et al., Autologous chondrocyte implantation at the knee using a bilayer collagen membrane with bone graft, 2005, pp. 330-332, vol. 87-B, The Journal of Bone & Joint Surgery [Br], London.
Bartlett, W., et al., Autologous chondrocyte implantation versus matrix-induced autologous chondrocyte implantation for osteochondral defects of the knee, 2005, pp. 641-645, vol. 87-B, No. 5, The Journal of Bone & Joint Surgery [Br], London.
Bassleer, C., et al., Human Chondrocytes in Tridimensional Culture, 1986, pp. 113-119, vol. 22, No. 3, Pt. 1, In Vitro Cellular & Developmental Biology, UK.
Behrens, Peter, et al., Matrix-associated autologous chondrocyte trnasplantation/implantation (MACT/MACI)—5-year follow-up, 2006, pp. 194-202, vol. 13, The Knee, Elsevier, UK.
Binette, F., et al., Terminally Redifferentiated Human Articular Chondrocytes Express Hyaline Cartilage Markers without Hypertrophy, 1997, p. 520, Genzyme Tissue Repair, 43rd Annual Meeting, Orthopaedic Research Society, USA.
Bujia, J., et al., Effect of Growth Factors on Cell Proliferation by Human Nasal Septal Chondrocytes Cultured in Monolayer, 1994, pp. 539-543, Acta Otolaryngol, vol. 114, Scandinavian University Press, Sweden.
Cherry, R.S., et al., Hydrodynamic effects on cells in agitated tissue culture reactors, 1986, pp. 29-41, Bioprocess Engineering, vol. 1, Springer-Verlag, USA.
Cherry, Robert S., et al., Physical Mechanisms of Cell Damage in Microcarrier Cell Culture Bioreactors, 1988, pp. 1001-1014, Biotechnology and Bioengineering, vol. 32, John Wiley & Sons, Inc., USA.
Cherry, Robert S., et al., Understanding and Controlling Fluid-Mechanical Injury of Animal Cells in Bioreactors, 1990, pp. 71-121, Animal Cell Biotechnology, vol. 4, Academic Press Limited, USA.
Cherubino, P., et al., Autologous chondrocyte implantation using a bilayer collagen membrane: A preliminary report, 2003, pp. 10-15, Journal of Orthopaedic Surgery vol. 11, No. 1, Italy.
Choi, Y. C., et al., Effect of Platelet Lysate on Growth and Sulfated Glycosaminoglycan Synthesis in Articular Chondrocyte Cultures, 1980, pp. 220-224, Arthritis and Rheumatism, vol. 22, No. 2, USA.
Coutts, Richard D., et al., Rib Periochondrial Autografts in Full-Thickness Articular Cartilage Defects in Rabbits, 1992, pp. 263-273, Clinic Orthopaedics and Related Research, No. 275, USA.
Croughan, Matthew S., et al., Hydrodynamic Effects on Animal Cells Grown in Microcarrier Cultures, 1987, pp. 130-141, Biotechnology and Bioengineering, vol. XXIX, John Wiley & Sons, Inc., USA.
Delbruck, Axel, et al., In-Vitro Culture of Human Chondrocytes from Adult Subjects, 1986, pp. 155-172, Connective Tissue Research, Gordon and Breach, Science Publishers, Inc., USA.
Dewey, C. F., Jr., et al., The Dynamic Response of Vascular Endothelial Cells to Fluid Shear Stress, 1981, pp. 177-185, Journal of Biomechnical Engineering, vol. 103, USA.
Dogterom, A.A., et al., Matrix depletion of young and old human articular cartilage by cultured autologous synovium fragments: a chondrocyte-independent effect, 1985, pp. 169-173, Rheumatology International, vol. 5, Springer-Verlag, UK.
Dowthwaite, Gary P., et al., The surface of articular cartilage contains a progenitor cell population, 2004, pp. 889-897, Journal of Cell Science, vol. 117, The Company of Biologists, 2004, UK.
Drobnic, M., M.D., M.Sc., et al., Comparison of four techniques for the fixation of a collagen scaffold in the human cadaveric knee, 2006, pp. 337-344, Osteoarthritis and Cartilage, vol. 14, Elsevier Ltd., UK.
Elima, Kati, et al., Expression of mRNAs for collagens and other matrix components in dedifferentiating and redifferentiating human chondrocytes in culture, 1989, pp. 195-198, FEBS Letters, vol. 258, No. 2, Elsevier Science Publishers B.V. (Biomedical Division), UK.
Evans, Robin C., et al., Solute diffusivity correlates with mechanical properties and matrix density of compressed articular cartilage, 2005, pp. 1-10, Archives of Biochemistry and Biophysics, vol. 442, Elsevier, UK.
Feder, Joseph, et al., The Large-Scale Cultivation of Mammalian Cells, 1983, pp. 6-43, Scientific American, vol. 248, No. 1, Scientific American, Inc., USA.
Frangos, John, et al., Flow Effects on Prostacyclin Production by Cultured Human Endothelial Cells, 1985, pp. 1477-1479, Science, vol. 227, Texas, USA.
Freed, L.E., et al., Neocartilage formation in vitro and in vivo using cells cultured on synthetic biodegradable polymers, 1993, pp. 11-23, Journal of Biomedical Materials Research, vol. 27, John Wiley & Sons, Inc., USA.
Freed, L.E., et al, Cultivation of Cell-Polymer Cartilage Implants in Bioreactors, 1993, pp. 257-264, Journal of Cellular Biochemistry, vol. 51, Wiley-Liss, Inc., USA.
Freed, L. E., et al., Composition of Cell-Polymer Cartilage Implants, 1994, pp. 605-614, Biotechnology and Bioengineering, vol. 43, John Wiley & Sons, Inc., USA.
Freed, L. E., et al., Cartilage Tissue Engineering Based on Cell-Polymer Constructs, 1995, pp. 1788-1806, Tissue Engineering of Cartilage, CRC Press, Inc., USA.
Freed, L. E., et al., Tissue engineering of cartilage in space, 1997, pp. 13885-13890, Proc. Natl. Acad. Sci., vol. 94, The National Academy of Sciences, USA.
Freed, L. E., et al., Cultivation of Cell-Polymer Tissue Constructs in Simulated Microgravity, 1995, pp. 306-313, Biotechnology and Bioengineering, vol. 46, John Wiley & Sons, Inc., USA.
Freed, L.E., et al., Cultivation of Cell-Polymer Cartilage Implants in Bioreactors, 1993, pp. 257-264, Journal of Cellular Biochemistry, vol. 51, Wiley-Liss, Inc. USA.

(56) References Cited

OTHER PUBLICATIONS

Fry, Donald, Acutte Vascular Endothelial Changes Associated with Increased Blood Velocity Gradients, 1968, pp. 165-197, Journal of the American Heart Association, vol. XXII, American Heart Association, USA.

FuB, M. et al., Characteristics of human chondrocytes, osteoblasts and fibroblasts seeded onto a type I/III collagen sponge under different culture conditions, 2000, pp. 303-310, Annals of Anatomy, vol. 182, Urban & Fischer Verlag, Germany.

Gille, J., et al., Migration pattern, morphology and viability of cells suspended in or sealed with fibrin glue: A histomorphologic study, 2005, pp. 339-348, Tissue and Cell, Vo. 37, Elsevier, UK.

Girotto, Davide, et al., Tissue-specific gene expression in chondrocytes grown on three-dimensional hyaluronic acid scaffolds, 2003, pp. 3265-3275, Biomaterials, vol. 24, Elsevier, UK.

Gooch, K.J., et al., Effects of Mixing Intensity on Tissue-Engineerd Cartilage, 2001, pp. 402-407, Biotechnology and Bioengineering, vol. 72, No. 4, John Wiley & Sons, Inc., USA.

Hollander, Anthony P., et al., Maturation of Tissue Engineered Cartilage Implanted in Injured and Osteoarthritic Human Knees, 2006, pp. 1787-1798, Tissue Engineering, vol. 12, No. 7, Mary Ann Leibert, Inc., UK.

Hu, Wei-Shou, Bioreactors for Animal Cell Cultivation, 1992, pp. 243-261, Recent Advances in Biotechnology, Kluwer Academic Publishers, Netherlands.

Kavalkovich, Karl W., et al., Chondrogenic Differentiation of Human Mesenchymal Stem Cells Within an Alginate Layer Culture System, 2002, pp. 457-466, In Vitro Cell. Dev. Biol.—Animal, vol. 38, Society for In Vitro Biology, USA.

Kimura, Tomoatsu, et al., Chondrocytes Embedded in Collagen Gels Maintain Cartilage Phenotype During Long-term Cultures, 1984, pp. 231-239, Clinical Orthopaedics and related Research, vol. 186, Japan.

Krueger, John W., et al., An In Vitro Study of Flow Response by Cells, 1971, pp. 31-36, Journal of Biomechanics, vol. 4, Pergamon Press, Great Britain.

Kuettner, Klaus E., et al, Synthesis of Cartilage Matrix by Mammalizn Chondrocytes in Vitro.I. Isolation, Culture Characteristics, and Morphology, 1982, pp. 743-750, The Journal of Cell Biology, vol. 93, The Rockefeller University Press, USA.

Kujawa, Mary J., et al., Hyaluronic Acid Bonded to Cell Culture Surfaces Inhibits the Program of Myogenesis, 1986, pp. 10-16, Developmental Biology, vol. 113, Academic Press, Inc., USA.

Kujawa, Mary J., et al., Substrate-Bonded Hyaluronic Acid Exhibits a Size-Dependent Stimulation of Chondrogenic Differentiation of Stage 24 Limb Mesenchymal Cells in Culture, 1986, pp. 519-528, Developmental Biology, vol. 114, Academic Press, Inc., USA.

Kujawa, Mary J., et al., Hyaluronic Acid Bonded to Cell-Culture Surfaces Timulates Chondrogenesis in Stage 24 Limb Mesenchyme Cell Cultures, 1986, pp. 504-518, Developmental Biology, vol. 114, Academic Press, Inc., USA.

Liu, Lin-Shu, et al., An osteoconductive collagen/hyaluronate matrix for bone regeneration, 1999, pp. 1097-1108, Biomaterials vol. 20, Elsevier, UK.

Lucas, Paul A., et al., Ectopic induction of cartilage and bone by water-soluble proteins from bovine bone using a collagenous delivery vehicle, 1989, pp. 23-39, Journal of Biomedical Materials Research: Applied Biomaterials, vol. 23, No. A1, John Wiley & Sons, Inc., USA.

Luyten, Frank P., et al., Articular Cartilage Repair: Potential Role of Growth and Differentiation Factors, pp. 227-236, Biological Regulation of the Chondrocytes, USA, 1992.

Marlovits, Stefan, et al., Early postoperative adherence of matrix-induced autologous chondrocyte implantation for the treatment of full-thickness cartilage defects of the femoral condyle, 2005, pp. 451-457, Knee Surg Sports Traumatol Arthrosc, vol. 13, Springer-Verlag, Austria.

Marlovits, S., et al., Correlation of MRI to clinical outcome scores after autologous chondrocyte transplantation: MOCART (Magnetic Resonance Observation of CArtilage Repair Tissue) granding and scoring system, 2007, B105, Osteoarthritis and Cartilage, vol. 15, Supplement B, p. 69, Austria.

McNickle, Allison G., et al., Overview of Existing Cartilage Repair Technology, 2008, pp. 196-201, Sports and Med Arthorosc Rev., vol. 16, No. 4, Lippincott Williams & Wilkins, USA.

McQueen, Anne, et al., Flow Effects on the Viability and Lysis of Suspended Mammalian Cells, 1987, pp. 831-836, Biotechnology Letters, vol. 9, No. 12, California Institute of Technology, USA.

Merchuk, Jose Celman, Shear Effects on Suspended Cells, 1988, pp. 65-95, Advances in Biochemical Engineering Biotechnology, vol. 44, Springer-Verlag Berlin Heidelberg.

Merchuk, Jose C., Why use air-lift bioreactors?, pp. 66-71, Tibtech, vol. 8, Elsevier Science Publishers Ltd., UK.

Mow, V. C., et al., Experimental Studies on Repair of Large Osteochondral Defects at a High Weight Bearing Area of the Knee Joint: A Tissue Engineering Study, 1991, pp. 198-207, Transactions of the ASME, Journal of Biomechanical Engineering, vol. 113, USA.

Nixon, Alan J., et al., Temporal matrix synthesis and histologic features of a chondrocyte-laden porous collagen cartilage analogue, 1993, pp. 349-356, American Journal of Veterinary Research, vol. 54, No. 2, USA.

O'Driscoll, Shawn W., et al., The Repair of Major Osteochondral Defects in Joint Surfaces by Neochondrogenesis with Autogenous Osteoperiosteal Grafts Stimulated by Continuous Passive Motion, 1986, pp. 131-140, Clinical Orthopaedics and Related Research, No. 208, Canada.

Papoutsakis, Eleftherios T., Fluid-mechanical damage of animal cells in bioreactors, 1991, pp. 427-437, TibTech, vol. 9, Elsevier Science Publishers Ltd. (UK).

Pavesio, Alessandra, et al., Hyaluronan-based scaffolds (Hyalograft C) in the treatment of knee cartilage defects: preliminary climical findings, 2003, pp. 203-217, Hyaluronan Scaffolds in Cartilage Repair, UK.

Robinson, Dror, et al., Regenerating Hyaline Cartilage in Articular Defects of Old Chickens Using Implants of Embryonal Chick Chondrocytes Embedded in a New Natural Delivery Substance, 1990, pp. 246-253, Calcified Tissue International, vol. 46, Springer-Verlag New York Inc., USA.

Ronga, Mario, et al., Arthroscopic Autologous Chondrocyte Implantation for the Treatment of a Chondral Defect in the Tibial Plateau of the Knee, 2004, pp. 79-84, Arthroscopy: The Journal of Arthroscopic and Related Surgery, vol. 20, No. 1, Italy.

Ronga, Mario, et al., Tissue Engineering Techniquest for the Treatment of a Comples Knee Injury, 2006, pp. 576.e1-576.e3, Arthroscopy: The Journal of Arthroscopic and Related Surgery, vol. 22, No. 5, Italy.

Russlies, M., et al., A cell-seeded biocompsite for cartilage repair, 2002, pp. 317-323, Annals of Anatomy, vol. 184, Urban & Fischer Verlag, UK.

Saini, Sunil, et al., Concentric Cylinder Bioreactor for Produciton of Tissue Engineered Cartilage: Effect of Seeding Density and Hydrodynamic Loading on Construct Development, 2003, pp. 510-521, Biotechnol. Prog., vol. 19, American Chemical Society and American Institute of Chemical Engineers, USA.

Salter, Robert B., The Biological Concept of Continuous Passive Motion of Synovial Joints: The First 18 Years of Basic Research and Its Clinical Application, 1990, pp. 335-353, Articular Cartilage and Knee Joint Function: Basic Science and Arthroscopy, Raven Press, Ltd., NY, USA.

Schmidt, Tannin A., et al., Synthesis of Proteoglycan 4 by Chondrocyte Subpopulations in Cartilage Explants, Monolayer Cultures, and Resurfaced Cartilage Cultures, 2004, pp. 2849-2857, Arthritis & Rheumatism, vol. 50, No. 9, American College of Rheumatology, USA.

Schwarz, Ray P., et al., Cell Culture for Three-Dimensional Modeling in Rotating-Wall Vessels: An Application of Simulated Microgravity, 1992, pp. 51-58, Journal of Tissue Culture Meth., Tissue Culture Association, TX, USA.

Shahgaldi, B. F., et al., Repair of Cartilage Lesions Using Biological Implants—A Comparative Histological and Biomechanical Study in Goats, 1991, pp. 57-64, Journal of Bone & Joint Surgery, vol. 73-5, UK.

(56) References Cited

OTHER PUBLICATIONS

Smith, R. Lane, et al., Effects of Fluid-Induced Shear on Articular Chondrocyte Morphology and Metabolism In Vitro, 1995, pp. 824-831, Journal of Orthopaedic Research, The Journal of Bone and Joint Surgery, Inc., vol. 13, USA.
Sohn, Stephen A., et al., Growth of Cartilage from a Free Perichondrial Graft Placed Across a Defect in a Rabbit's Trachea, 1974, pp. 55-60, Plastic & Reconstructive Surgery, vol. 53, No. 1, Lippincott Williams & Wilkins, USA.
Stathopoulos, N.A., et al., Shear Stress Effects on Human Embryonic Kidney Cells In Vitro, 1985, pp. 1021-1026, Biotechnology and Bioengineering, vol. XXVII, John Wiley & Sons, Inc., USA.
Trattnig, Siegfried, et al., Matrix-based autologous chondrocyte implantation for cartilage repair: noninvasive monitoring by high-resolution magnetic resonance imaging, 2005, pp. 779-787, Magnetic Resonance Imaging, vol. 23, Elsevier, Austria.
Vacanti, C.A., et al., Synthetic Polymers Seeded with Chondrocytes Provide a Template for New Cartilage Formation, 1991, pp. 753-759, Plastic and Reconstructive Surgery, vol. 88, No. 5, USA.
Venkat, Raghavan, V., et al., Study of Hydrodynamics in Microcarrier Culture Spinner Vessels: A Particle Tracking Velocimetry Approach, 1996, pp. 456-466, Biotechnology and Bioengineering, vol. 49, John Wiley & Sons, Inc., USA.
Oldshue, James Y., et al., Comparison of Mass TRansfer Characteristics of Radial & Axial Flow Impellers, 1988, pp. 345-350, 6th European Conference on Mixing, Springer-Verlag, UK.
Willers, Craig, et al., Articular cartilage repair: procedures versus products, 2007, pp. 373-392, Expert Rev. Med. Devices, vol. 4., No. 3, Future Drugs Ltd, US.
Yoshihashi, Yuji, Tissue Reconstitution by Isolated Artcular Chondrocytes in vitro, 1983, pp. 629-641, The Journal of Japanese Orthopaedic Surgical Society, vol. 58, Japan.
"U.S. Appl. No. 13/447,356, Response filed Oct. 10, 2012 to Restriction Requirement mailed Sep. 10, 2012", 6 pgs.
"U.S. Appl. No. 13/447,356, Restriction Requirement mailed Sep. 10, 2012", 7 pgs.
"European Application Serial No. 04713503.3, Office Action mailed Aug. 12, 2009", 5 pgs.
"European Application Serial No. 04713503.3, Response filed Feb. 11, 2010 to Office Action mailed Aug. 12, 2009", 8 pgs.
"European Application Serial No. 04713503.3, Response filed Mar. 15, 2012 to Summons to Attend Oral Proceeding mailed Dec. 13, 2011", 46 pgs.
"European Application Serial No. 04713503.3, Response filed Apr. 4, 2012", 26 pgs.
"European Application Serial No. 04713503.3, Summons to Attend Oral Proceedings mailed Dec. 13, 2011", 5 pgs.
"Japanese Application Serial No. 2008-531502, Office Action mailed May 22, 2012", With English Translation, 7 pgs.
Degroot, Jeroen, et al., "Age Related Decrease in Proteoglycan Synthesis of Human Articular Chondrocytes", The Role of Nonenzymatic Glycation Arthritis and Rheumatism, vol. 42, No. 5,, (May 1999), 1003-1009.
Feder, Joseph, et al., "The Promise of Chondral Repair Using Neocartilage", Chapter 22, (2004), 219-226.
Morales, T. I., "Condrocyte moves: clever strategies?", Osteoarthritis and Cartilage 15, (2007), 861-871.
Namba, Robert S., "Spontaneous Repair of Superficial Defects in Articular Cartilage in a Fetal Lamb Model", Journal of Bone and Joint Surgery, Inc., (1998), 4-10.
Sengupta, S, et al., "The Fate of Transplants of Articular Cartilage in the Rabbit", JBJS, vol. 56B, No. 1, (1974), 167-177.
Specchia, Nicola, et al., "Fetal Chondral Homographs in the Repair of Articular Cartilage Defects", Bulletin of the Hospital for Joint Diseases vol. 54 (4), (1996), 230-235.
Williamson, Amanda K, et al., "Compressive Properties and Function-composition relationships of developing bovine articular cartilage", Journal of Orthopaedic Research vol. 19, (2001), 1113-1121.

Zuger, B J, et al., "Laser solder welding of articular cartilage: tensile strength and chondrocyte viability.", Lasers in Surgery and Medicine vol. 28, No. 5, XP002285204 ISSN: 0196-8092, 427-434.
"Australian Application Serial No. 2006294351, First Examiner Report mailed Aug. 3, 2011", 1 pg.
"European Application Serial No. 05405547.0, European Search Report mailed Jun. 2, 2006", 6 pgs.
"European Application Serial No. 06775196.6, Office Action mailed Feb. 24, 2009", 4 pgs.
"European Application Serial No. 06775196.6, Response filed Aug. 13, 2009 to Office Action mailed Feb. 24, 2009", 10 pgs.
"International Application Serial No. PCT/CH2006/000503, International Search Report mailed Jan. 18, 2007", 2 pgs.
"International Application Serial No. PCT/CH2006/000503, Written Opinion mailed Jan. 18, 2007", 5 pgs.
Chen, A. C., et al., "Chondrocyte Transplantation to Articular Cartilage Explants In Vitro", Journal of Orthopaedic Research, 15, (1997), 791-802.
Kurtis, M. S., et al., "Integrin-mediated Adhesion of Human Articular Chondrocytes to Cartilage", Arthritis & Rheumatism, 48(1), (2003), 110-118.
Schinagl, et al., "Effect of Sedding Duration on the Strength of Chondrocyte Adhesion to Articular Cartilage", Jounral of Orthopaedic Research, 17, (1999), 121-129.
"U.S. Appl. No. 10/129,915, Response filed Oct. 14, 2008 to Final Office Action mailed Aug. 22, 2008", 8 pgs.
"U.S. Appl. No. 10/129,915, Response filed Oct. 17, 2005 to Restriction Requirement mailed Oct. 11, 2005", 1 pg.
"U.S. Appl. No. 10/129,915, Response filed Oct. 24, 2006 to Final Office Action mailed Aug. 16, 2006", 5 pgs.
"U.S. Appl. No. 10/129,915, Response filed Nov. 24, 2008 to Restriction Requirement mailed Oct. 29, 2008", 8 pgs.
"U.S. Appl. No. 10/129,915, Response to Ex Parte Quayle Action filed Aug. 30, 2011", 6 pgs.
"U.S. Appl. No. 10/129,915, Restriction Requirement mailed May 6, 2008", 5 pgs.
"U.S. Appl. No. 10/129,915, Restriction Requirement mailed Oct. 11, 2005", 5 pgs.
"U.S. Appl. No. 10/129,915, Restriction Requirement mailed Oct. 29, 2008", 3 pgs.
"U.S. Appl. No. 10/386,946, Non Final Office Action mailed May 19, 2004", 5 pgs.
"U.S. Appl. No. 10/386,946, Non Final Office Action mailed Jul. 27, 2005", 5 pgs.
"U.S. Appl. No. 10/386,946, Notice of Allowance mailed Jan. 13, 2005", 6 pgs.
"U.S. Appl. No. 10/386,946, Preliminary Amendment filed Jul. 21, 2003", 6 pgs.
"U.S. Appl. No. 10/386,946, Response filed Oct. 12, 2004 to Non Final Office Action mailed May 19, 2004", 2 pgs.
"U.S. Appl. No. 10/413,000, Non Final Office Action mailed Oct. 18, 2005", 5 pgs.
"U.S. Appl. No. 10/413,000, Notice of Allowance mailed Apr. 4, 2006", 4 pgs.
"U.S. Appl. No. 10/413,000, Response filed Jan. 18, 2006 to Non Final Office Action mailedOct. 18, 2005", 5 pgs.
"U.S. Appl. No. 10/413,000, Supplemental Notice of Allowability mailed May 15, 2006", 4 pgs.
"U.S. Appl. No. 10/547,437, Advisory Action mailed Mar. 15, 2011", 3 pgs.
"U.S. Appl. No. 10/547,437, Advisory Action mailed Apr. 27, 2010", 4 pgs.
"U.S. Appl. No. 10/547,437, Advisory Action mailed Jul. 7, 2009", 3 pgs.
"U.S. Appl. No. 10/547,437, Advisory Action mailed Aug. 20, 2008", 3 pgs.
"U.S. Appl. No. 10/547,437, Appeal Brief filed Jul. 12, 2010", 28 pgs.
"U.S. Appl. No. 10/547,437, Final Office Action mailed Feb. 12, 2010", 32 pgs.
"U.S. Appl. No. 10/547,437, Final Office Action mailed Apr. 29, 2009", 22 pgs.
"U.S. Appl. No. 10/547,437, Final Office Action mailed May 29, 2008", 17 pgs.

(56) References Cited

OTHER PUBLICATIONS

"U.S. Appl. No. 10/547,437, Final Office Action mailed Dec. 10, 2010", 16 pgs.

"U.S. Appl. No. 10/547,437, Non Final Office Action mailed Jan. 4, 2008", 17 pgs.

"U.S. Appl. No. 10/547,437, Non Final Office Action mailed Aug. 13, 2010", 27 pgs.

"U.S. Appl. No. 10/547,437, Non Final Office Action mailed Aug. 20, 2009", 24 pgs.

"U.S. Appl. No. 10/547,437, Non Final Office Action mailed Dec. 24, 2008", 24 pgs.

"U.S. Appl. No. 10/547,437, Notice of Allowance mailed Jan. 10, 2012", 5 pgs.

"U.S. Appl. No. 10/547,437, Notice of Allowance mailed Sep. 26, 2011", 5 pgs.

"U.S. Appl. No. 10/547,437, Preliminary Amendment filed Aug. 25, 2005", 12 pgs.

"U.S. Appl. No. 10/547,437, Response filed Mar. 10, 2011 to Final Office Action mailed Dec. 10, 2010", 12 pgs.

"U.S. Appl. No. 10/547,437, Response filed Mar. 24, 2009 to Non Final Office action mailed Dec. 24, 2008", 11 pgs.

"U.S. Appl. No. 10/547,437, Response filed Mar. 27, 2008 to Non Final Office Action mailed Jan. 4, 2008", 17 pgs.

"U.S. Appl. No. 10/547,437, Response filed Apr. 12, 2010 to Final Office Action mailed Feb. 12, 2010", 13 pgs.

"U.S. Appl. No. 10/547,437, Response filed Jun. 23, 2009 to Final Office Action mailed Apr. 29, 2009", 12 pgs.

"U.S. Appl. No. 10/547,437, Response filed Jul. 24, 2008 to Final Office Action mailed May 29, 2008", 20 pgs.

"U.S. Appl. No. 10/547,437, Response filed Nov. 15, 2010 to Non Final Office Action mailed Aug. 13, 2010", 14 pgs.

"U.S. Appl. No. 10/547,437, Response filed Dec. 18, 2009 to Non Final Office Action mailed Aug. 20, 2009", 14 pgs.

"U.S. Appl. No. 11/046,674, Appeal Brief filed Nov. 9, 2006", 33 pgs.

"U.S. Appl. No. 11/046,674, Examiner's Answer to Appeal Brief Feb. 13, 2007", 18 pgs.

"U.S. Appl. No. 11/046,674, Final Office Action mailed Mar. 23, 2006", 12 pgs.

"U.S. Appl. No. 11/046,674, Final Office Action mailed Aug. 9, 2006", 14 pgs.

"U.S. Appl. No. 11/046,674, Non Final Office Action mailed Jan. 8, 2009", 6 pgs.

"U.S. Appl. No. 11/046,674, Non Final Office Action mailed Aug. 12, 2005", 12 pgs.

"U.S. Appl. No. 11/046,674, Notice of Allowance mailed Apr. 14, 2008", 6 pgs.

"U.S. Appl. No. 11/046,674, Notice of Allowance mailed Sep. 15, 2009", 7 pgs.

"U.S. Appl. No. 11/046,674, Preliminary Amendment filed Jan. 28, 2005", 3 pgs.

"U.S. Appl. No. 11/046,674, Reply Brief filed Apr. 2, 2007", 4 pgs.

"U.S. Appl. No. 11/046,674, Response filed May 5, 2009 to Non Final Office Action mailed Jan. 8, 2009", 24 pgs.

"U.S. Appl. No. 11/046,674, Response filed Jun. 2, 2006 to Final Office Action mailed Mar. 23, 2006", 8 pgs.

"U.S. Appl. No. 11/046,674, Response filed Dec. 8, 2005 to Non Final Office Action mailed Aug. 12, 2005", 13 pgs.

"U.S. Appl. No. 11/433,968, Advisory Action mailed Jun. 27, 2008", 3 pgs.

"U.S. Appl. No. 11/433,968, Non Final Office Action mailed May 14, 2008", 8 pgs.

"U.S. Appl. No. 11/433,968, Non Final Office Action mailed Sep. 11, 2007", 9 pgs.

"U.S. Appl. No. 11/433,968, Non Final Office mailed Nov. 12, 2008", 10 pgs.

"U.S. Appl. No. 11/433,968, Preliminary Amendment filed May 15, 2006", 7 pgs.

"U.S. Appl. No. 11/433,968, Response filed Feb. 15, 2008 to Non Final Office Action mailed Sep. 11, 2007", 12 pgs.

"U.S. Appl. No. 11/433,968, Response filed May 27, 2008 to Final Office Action mailed May 14, 2008", 3 pgs.

"U.S. Appl. No. 11/997,769, Final Office Action mailed Dec. 30, 2010", 6 pgs.

"U.S. Appl. No. 12/463,108, Final Office Action mailed Dec. 5, 2011", 9 pgs.

"U.S. Appl. No. 12/463,108, Non Final Office Action mailed Mar. 28, 2011", 9 pgs.

"U.S. Appl. No. 12/463,108, Preliminary Amendment filed May 8, 2009", 6 pgs.

"U.S. Appl. No. 12/463,108, Preliminary Amendment filed Aug. 12, 2009", 4 pgs.

"U.S. Appl. No. 12/463,108, Response filed Sep. 28, 2011 to Non Final Office Action mailed Mar. 28, 2011", 9 pgs.

"U.S. Appl. No. 12/657,242, Examiner Interview Summary mailed Feb. 4, 2011", 4 pgs.

"U.S. Appl. No. 12/657,242, Non Final Office Action mailed Apr. 18, 2011", 9 pgs.

"U.S. Appl. No. 12/657,242, Preliminary Amendment filed Jan. 15, 2010", 10 pgs.

"Australian Application Serial No. 11249/01, Office Action mailed May 14, 2004", 4 pgs.

"Australian Application Serial No. 11249/01, Office Action mailed Nov. 25, 2005", 2 pgs.

"Australian Application Serial No. 11249/01, Response filed Nov. 18, 2005 to Office Action mailed May 14, 2004", 13 pgs.

"Australian Application Serial No. 11249/01, Response filed Dec. 19, 2005 to Office Action mailed Nov. 25, 2005", 4 pgs.

"Australian Application Serial No. 2004216551, Office Action mailed May 21, 2008", 2 pgs.

"Australian Application Serial No. 2004216551, Office Action mailed Nov. 8, 2007", 3 pgs.

"Australian Application Serial No. 2004216551, Response filed Apr. 9, 2008 to Office Action mailed Nov. 8, 2007", 3 pgs.

"Australian Application Serial No. 2004216551, Response filed Aug. 27, 2008 to Office Action mailed May 21, 2008", 11 pgs.

"Australian Application Serial No. 2004216551, Statement of Proposed Amendments mailed May 6, 2008", 4 pgs.

"Canadian Application Serial No. 2,300,415, Office Action mailed Jan. 2, 2008", 2 pgs.

"Canadian Application Serial No. 2,300,415, Office Action mailed Aug. 8, 2006", 1 pg.

"Canadian Application Serial No. 2,300,415, Office Action mailed Nov. 8, 2006", 4 pgs.

"Canadian Application Serial No. 2,300,415, Response filed Jun. 10, 2008 to Office Action mailed Jan. 2, 2008", 8 pgs.

"Canadian Application Serial No. 2,300,415, Response filed Aug. 11, 2008 to Office Action mailed Aug. 6, 2008", 9 pgs.

"Canadian Application Serial No. 2,362,600, Office Action mailed Apr. 25, 2008", 4 pgs.

"Canadian Application Serial No. 2,362,600, Office Action mailed Jun. 2, 2009", 7 pgs.

"Canadian Application Serial No. 2,362,600, Office Action mailed Jul. 2, 2010", 7 pgs.

"Canadian Application Serial No. 2,362,600, Response filed Oct. 24, 2008 to Office Action mailed Apr. 24, 2008", 31 pgs.

"Canadian Application Serial No. 2,362,600, Response filed Dec. 1, 2009 to Office Action mailed Jun. 2, 2009", 14 pgs.

"Canadian Application Serial No. 2,390,834, Office Action mailed Mar. 11, 2009", 3 pgs.

"Canadian Application Serial No. 2,390,834, Office Action mailed May 11, 2010", 4 pgs.

"Canadian Application Serial No. 2,390,834, Response filed Sep. 11, 2009 to Office Action mailed Mar. 11, 2009", 10 pgss.

"European Application Serial No. 00972527.6, Office Action mailed Dec. 12, 2002", 2 pgs.

"European Application Serial No. 00972527.6, Response filed Mar. 27, 2003 to Office Action mailed Dec. 13, 2002", 6 pgs.

"European Application Serial No. 97810567.4, Office Action mailed Feb. 6, 2001", 3 pgs.

"European Application Serial No. 97810567.4, Partial European Search Report mailed Feb. 2, 1998", 2 pgs.

(56) References Cited

OTHER PUBLICATIONS

"European Application Serial No. 97810567.4, Response filed Aug. 8, 2001 to Office Action mailed Feb. 6, 2001", 8 pgs.
"European Application Serial No. 97922797.2, Office Action mailed Dec. 27, 2001", 2 pgs.
"European Application Serial No. 97922797.2, Response filed Apr. 12, 2002 to Office Action mailed Dec. 27, 2001", 6 pgs.
"European Application Serial No. 99122460.1, European Search Report mailed Jul. 19, 2000", 4 pgs.
"How INFUSE Bone Graft Works", Medtronic, [Online]. Retrieved from the Internet. <http://www.infusebonegraft.com/how_infuse_works_trauma.html, (Retrieved Apr. 24, 2007), 4 pgs.
"Information for Patients: Understanding OP-1 Putty", Stryker, [Online]. Retrieved from the Internet. <http://www.stryker.com/orthobiologics/us/patients/spine/understandingop1putty.html>, (Accessed Apr. 24, 2007), 1 pg.
"International Application Serial No. 00915782.7, Office Action mailed Oct. 25, 2006", 8 pgs.
"International Application Serial No. 00915782.7, Response filed Apr. 24, 2007 to Office Action mailed Oct. 25, 2006", 7 pgs.
"International Application Serial No. 00915782.7, Supplementary European Search Report mailed Jun. 21, 1966", 2 pgs.
"International Application Serial No. PCT/ US2000/03972, Preliminaary Search Report mailed Mar. 25, 2001", 4 pgs.
"International Application Serial No. PCT/CH2000/000602, International Preliminary Examination Report mailed Feb. 18, 2002", 6 pgs.
"International Application Serial No. PCT/CH2000/000602, International Search Report mailed Jan. 26, 2001", 3 pgs.
"International Application Serial No. PCT/CH2000/000602, Written Opinion mailed Dec. 4, 2001", 5 pgs.
"International Application Serial No. PCT/CH2004/000093, International Preliminary Report on Patentability mailed Aug. 26, 2005", 7 pgs.
"International Application Serial No. PCT/CH2004/000093, International Search Report and Written Opinion mailed Jun. 21, 2004", 10 pgs.
"International Application Serial No. PCT/EP98/05100, International Search Report mailed Jan. 22, 1999", 4 pgs.
"International Application Serial No. PCT/US2000/03972, International Search Report mailed Aug. 11, 2000", 2 pgs.
"Japanese Application Serial No. 1998-0500061, Office Action mailed Jun. 21, 2005", 4 pgs.
"Japanese Application Serial No. 1998-0500061, Office Action mailed Nov. 2, 2004", 9 pgs.
"Japanese Application Serial No. 1998-0500061, Response filed May 2, 2004 to Office Action mailed Nov. 2, 2004", 66 pgs.
"Japanese Application Serial No. 2000-509464, Office Action mailed Apr. 14, 2009", 4 pgs.
"Japanese Application Serial No. 2000-509464, Office Action mailed Jul. 6, 2010", 10 pgs.
"Japanese Application Serial No. 2000-509464, Response filed Jul. 19, 2009", 15 pgs.
"Japanese Application Serial No. 2000-599344, Office Action mailed Apr. 17, 2012", 3 pgs.
"Japanese Application Serial No. 2000-599344, Office Action mailed Sep. 1, 2009", 11 pgs.
"Japanese Application No. 2000-599344, Office Action mailed Nov. 11, 2008 09-0", 11 pgs.
"Japanese Application Serial No. 2000-599344, Office Action mailed Nov. 27, 2007", 7 pgs.
"Japanese Application Serial No. 2000-599344, Office Action Mailed Apr. 17, 2012", English Translation, 4 Pgs.
"Japanese Application Serial No. 2000-599344, Response filed Feb. 10, 2009", 7 pgs.
"Japanese Application Serial No. 2000-599344, Response filed Apr. 28, 2008", 7 pgs.
"Japanese Application Serial No. 2001-536163, Final Office Action mailed Feb. 14, 2012", 1 pgs.
"Japanese Application Serial No. 2001-536163, Non Final Office Action mailed Jan. 25, 2011", (with English Translation), 5 pgs.
"Japanese Application Serial No. 2001-536163, Office Action mailed Jun. 28, 2011", (with English Translation), 8 pgs.
"Japanese Application Serial No. 2001-536163, Response filed Apr. 25, 2011 to Non Final Office Action mailed Jan. 25, 2011", (with English Translation), 4 pgs.
"Japanese Application Serial No. 2001-536163, Response filed Nov. 24, 2011 to Office Action mailed Jun. 28, 2011", 6 pgs.
Adkisson, H. Davis, et al., "The Potential of Human Allogeneic Juvenile Chondrocytes for Restoration of Articular Cartilage", The American Journal of Medicine vol. 38, (Apr. 27, 2010), 1324-1333.
Alpasian, C., et al., "Long-term evaluation of recombinant human bone morphogenic protein-2 induced bone formation with a biologic and synthetic delivery system", British Journal of Oral and Maxoffacial Surgery, 34, (1996), 414-418.
Baragi, et al., "Transplantation of adenvirally transduced allogeneic chondrocytes into articular cartilage defects in vivo", Osteoarthritis and cartilage, vol. 5, (1997), 275-282.
Blanco, M. D., et al., "Development and characterization of protein-loaded poly (lactideco-glycolide) nanospheres", European Journal of Pharmaceutics and Biopharmaceutics, 43(3), (1997), 287-294.
Boden, S. D., et al., "In Vivo Evaluation of a Resorbable Osteoinductive Composite as a Graft Substitute for Lumbar Spinal Fusion", Journal of Spinal Disorders 10(1), (1997), 1-11.
Cheung, H, et al., "Growth of osteoblasts on porous calcium phosphate ceramic: an in vitro model for biocompatibility study", Biomaterials vol. 10, Issue 1, (Jan. 1989), 63-67.
Cornell, et al., "A biosensor that uses ion-channel switches", Nature vol. 387, (Jun. 1997), 580-583.
Damien, C. J., et al., "A Composite of Natural Coral, Collagen, Bone Protein and Basic Fibroblast Growth Factor Tested in a Rat Subcutaneous Model", Annales Chirurgiae et Gynaecologiae Suppl, 207, (1993), 117-128.
Duggirala, S. S., et al., "Interaction of Recombinant Human Bone Morphogenic Protein-2 with Poly (d,l, Lactide-co-glycolide) Microspheres", Pharmaceutical Development and Technology, 1(1), (1996), 11-19.
Duggirala, S. S., et al., "The Evaluation of Lyophilized Polymer Matrices for Administering Recombinant Human Bone Morphogenic Protein-2", Pharmaceutical Development and Technology 1(2), (1996), 165-174.
Hollinger, Jeffrey O., et al., "Poly(alpha-hydroxy acids): carriers for bon morphogenetic proteins", Biomaterial, vol. 17, (1996), 187-194.
Kenley, R., et al., "Osseous regeneration in the rat calvarium using novel delivery systems for recombination human bone morphogenic protein-2 (rhBMP-2)", Journal of Biomedical Materials Research, vol. 28, (1994), 1139-1147.
Kim, Young IL, et al., "The antihypertensive effect of orally administered nifedipine-loaded nanoparticles in spontaneously hypertensive rats", Br J Pharmacol., 120(3), (Jan. 23, 1997), 399-404.
Lee, S. C., et al., "Healing of large segmental defects in rat femurs is aided by RhBMP-2 in PLGA matrix", Journal of Biomedical Materials Research, 28(10), (1994), 1149-1156.
Mathiowitz, Edith, et al., "Biologically erodable microspheres as potential oral drug delivery systems", Nature, vol. 386, (Mar. 1997), 410-414.
Pollok, et al., "Long term insulin-secretory function of islets of Langerhans encapsulated with a layer of confluent chondrocytes for immunoisolation", Pediatric Surg Int, vol. 15, (1999), 164-167.
Pollok, J. M., et al., "Immunoisolation of xenogeneic islets using a living tissue engineered cartilage barrier", Transplantation Proceedings, 29(4), (1997), 2131-2133.
Sittinger, M, et al., "Encapsulation of artificial tissues in polyelectrolyte complexes: preliminary studies", Biomaterials 17(10), (1996), 3 pgs.
Sittinger, M, et al., "Engineering of cartilage tissue using bioresorbable polymer carriers in perfusion culture", Biomaterials 15(6), (1994), 451-6.

(56) References Cited

OTHER PUBLICATIONS

Song, C. X, et al., "Formulation and Characterization of Biodegradable Nanoparticles for Intravascular Local Drug Delivery", Journal of Controlled Release vol. 43, No. 2/03,, XP00632668, (Jan. 18, 1997), 197-212.
"U.S. Appl. No. 13/447,356, Final Office Action mailed Apr. 9, 2013", 11 pgs.
"U.S. Appl. No. 13/447,356, Non Final Office Action mailed Nov. 2, 2012", 10 pgs.
"U.S. Appl. No. 13/447,356, Response filed Apr. 2, 2013 to Non-Final Office Action mailed Nov. 2, 2012", 9 pgs.
"U.S. Appl. No. 13/447,356, Examiner Interview Summary mailed Jul. 16, 2013", 4 pgs.
"U.S. Appl. No. 13/447,356, Examiner Interview Summary mailed Jul. 19, 2013", 4 pgs.
Du, C., et al., "Formation of calcium phosphate/collagen composites through mineralization of collagen matrix", J Biomed Mater Res., 50(4), (Jun. 15, 2000), 518-27.
"European Application Serial No. 06775196.6, Examination Notification Art. 94(3) mailed Jul. 25, 2013", 5 pgs.

\* cited by examiner

IMPLANT FOR THE REPAIR OF A CARTILAGE DEFECT AND METHOD FOR MANUFACTURING THE IMPLANT

This application is the national phase of international application PCT/CH2006/000503, which was filed on Sep. 18, 2006, and claims priority of European application 05405547.0, which was filed on Sep. 20, 2005.

The invention belongs to the field of medical technology and concerns an implant for the repair of a cartilage defect in a human or animal patient, in particular for the repair of a full thickness defect in articular cartilage. The invention further concerns a method for manufacturing the implant.

A plurality of known methods for the repair of cartilage defects make use of cells originating from the patient, i.e. of autologous cells, in particular autologous chondrocytes or autologous cells having a chondrogenic potential. These cells are thought to be able (possibly only after further differentiation) to produce and maintain in vivo or in vitro a cartilage matrix which is similar to the endogenous cartilage and/or to be able to connect, with the help of such a matrix, an implant with the endogenous cartilage and/or bone tissue being situated around the defect.

The publication U.S. Pat. No. 4,846,835 (Grande) proposes to bring a suspension of autologous into an articular cartilage defect, and to close the defect by suturing a piece of periosteum over the defect for keeping the cells in the defect where they are supposed to produce cartilage tissue (in vivo) and to connect this tissue at the same time with the surrounding endogenous cartilage or bone tissue. A plurality of further publications (e.g., WO-2004/00093, Centerpulse Biologics) propose to seed the cells in a porous or fibrous body serving as a scaffold (e.g., collagen sponge) and to cultivate the scaffold with the cells in vitro at least until the cells are attached on inner surfaces of the scaffold, and to then position the scaffold with the cells in the defect and fastening it in the defect with suitable means.

In the above named publication WO-2004/00093 (Centerpulse Biologics) it is further proposed to introduce different cells in different areas of the scaffold, wherein, for example, the cells which are originally used are cells having a chondrogenic potential (cells of a stem cell nature or de-differentiated chondrocytes). Firstly, cells are only seeded in an inner area of the scaffold and the scaffold is then cultured in vitro such that the cells are differentiated or re-differentiated to chondrocytes and start producing a cartilage matrix. Only then the outer or edge areas of the scaffold are seeded with the same cells as used for seeding the inner area, whereupon the scaffold is implanted in the defect such that the outer areas containing the later introduced and therefore less differentiated cells come into contact with the healthy tissue surrounding the defect. The principle of using cells of a lower differentiation state in the outer areas of the scaffold is based on the finding that not fully differentiated chondrocytes are better suitable for assisting in the integration of the implant in the defect. Possibly such finding is due to the fact that these not fully differentiated cells have more capabilities for migrating and multiplying than fully differentiated chondrocytes and are better equipped for taking over functions regarding a healing process.

The publication WO-97146665 (Sulzer Orthopedics) proposes to produce cartilage tissue in an in vitro three dimensional tissue culture, for example, from autologous chondrocytes, wherein, before the tissue culture, the chondrocytes are usually proliferated in vitro and wherein no artificial scaffold is used. Therein, the in vitro proliferated and thereby de-differentiated chondrocytes are re-differentiated during tissue culture and the matrix produced by these cells is very similar to a natural cartilage matrix. The cartilage tissue resulting from the in vitro tissue culture is then positioned in a cartilage defect and is fastened therein with suitable means.

The publication U.S. Pat. No. 6,662,805 (Johns Hopkins University, Chondros Inc.) proposes to proliferate chondrocytes on support particles, to then form an aggregation of such populated particles and to implant the aggregate in the cartilage defect, wherein a suspension of further cells is introduced between the implant and endogenous cartilage or possibly bone surrounding the defect. The cells in the particle aggregate are e.g. chondrocytes and the cells in the suspension are cells derived in vitro from stem cells being therefore able to be further differentiated to become cells of a chondrogenic, fibroblastic, myoblastic or osteoblastic phenotype. This means that here also differentiated chondrocytes are used within the implant and less differentiated cells in the area between implant and endogenous tissue surrounding the implant.

It is the object of the invention to create an implant comprising viable cells and being suitable to be used for repairing a cartilage defect, in particular a full thickness defect in articular cartilage, wherein integration of the implant in the endogenous tissue is to be very good, wherein it is to be possible to manufacture the implant from only autologous materials and wherein it is to be possible to implant the implant using known and approved implantation methods. It is a further object of the invention to create a method for manufacturing the implant.

This object is achieved by the implant and the method for manufacturing the implant as defined in the patent claims.

An implant according to the invention comprises an implant body consisting of a natural cartilage matrix in which the chondrocytes which originally produced the matrix are present in a viable and/or non-viable state. Further cells adhere to the surface of the implant body, these surface cells having a chondrogenic potential (i.e., being not fully differentiated chondrocytes but having the capability to be differentiated or to be re-differentiated to fully differentiated chondrocytes. Therein the matrix has no relevant porosity and the surface cells are advantageously autologous cells.

An implant according to one embodiment of the invention serves for repairing a defect in articular cartilage and comprises an implant body shaped as a relatively thin disk or plate having a form which is adapted to the form of the defect, wherein the thickness of the disk is not greater than the thickness of the articular cartilage to be repaired. On both opposite sides of the disk-shaped implant body there are surface cells adhering, which surface cells are e.g., autologous cells. Surface cells possibly also adhere to the narrow sides of the implant body and possibly also on inner surfaces of openings which extend into and/or trough the implant body. If an implant according to another embodiment of the invention is to serve for repairing another cartilage defect, the implant body is of a shape adapted to this defect.

An implant according to a preferred embodiment of the invention comprises an implant body consisting of cartilage tissue produced by in vitro tissue culturing starting from autologous cells, which cartilage tissue does not contain any artificial or immunogenic matrix material and in which cartilage tissue the chondrocytes are in a viable state. The also autologous surface cells adhering to surfaces of the implant body are e.g. de-differentiated chondrocytes produced by in vitro proliferation starting from autologous chondrocytes. In the same manner, stem cells harvested from bone marrow or cells having a chondrogenic potential and being harvested from other tissue may be adhered to the implant body surfaces.

An implant according to the preferred embodiment of the invention is e.g. produced in the following manner. Chondrocytes are isolated from a cartilage biopsy harvested from the patient. The isolated chondrocytes are proliferated in vitro in a monolayer culture (step of in vitro cell proliferation) whereby they are de-differentiated. A first part of the proliferated cells are grown into a cartilage tissue in an in vitro tissue culture under conditions suitable for re-differentiation of the cells and for growth of a three dimensional tissue piece (step of in vitro tissue culturing). The other part of the proliferated cells are maintained in the de-differentiated state, e.g. by freezing. In a last step, the implant body consisting of the in vitro produced cartilage tissue piece is cultured in a suspension of the de-differentiated cells (step of implant coating) until the de-differentiated cells adhere to the implant body surface. The implant prepared in the above described steps is then implanted in the defect in a per se known manner and is possibly fastened to adjacent tissue(s) with suitable means.

As alternative and/or in addition to a piece of cartilage tissue grown in an in vitro tissue culture, autologous cartilage tissue harvested from the patient or cartilage tissue produced by in vitro culture starting from donor chondrocytes, or allogeneic and/or xenogeneic cartilage tissue explants may be used as an implant body for the implant according to the invention. If the implant body consists of non-autologous but homologous or xenogeneic cartilage tissue it may be advantageous to kill the chondrocytes which are integrated in the tissue, before the step of implant coating. In any case, before implantation, the implant body is cultured in vitro in a suspension of the further cells (autologous cells having a chondrogenic potential) until these further cells adhere to possibly all surfaces of the implant body and as little cells as possible remain suspended. It is also possible to culture a plurality of parts of an implant body separately in a suspension of the further cells (preliminary step of coating) and to then bring the preliminarily coated parts in touch with each other and subject them to a final step of coating, wherein the implant body parts are connected to each other by the surface cells adhered in the preliminary step of coating to such a degree that the assemblage of parts can be handled in the same manner as a one-piece implant.

Implants according to exemplary embodiments of the invention and of the method for manufacturing such implants are described in detail in connection with the following Figures, wherein.

Figure 1:
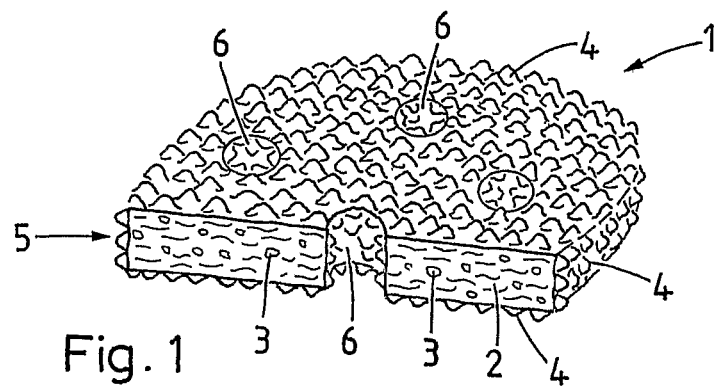
FIG. 1 is a schematic section of an implant according to one embodiment of the invention and being suitable for the repair of an articular cartilage defect in a human or animal patient.

FIG. 1 shows an implant according to one embodiment of the invention which is suitable for the repair of an articular cartilage defect. The implant comprises a disk-shaped implant body 2 which is shown in section. The implant body comprises natural cartilage tissue, i.e. a matrix produced by chondrocytes and including collagen and proteoglycans, in which matrix chondrocytes 3 are integrated. The chondrocytes 3 are autologous and in a viable state, or they are homologous or xenogeneic and, depending on their immunogenicity, in a viable and/or non-viable state. The surface of the implant body 2 is coated or seeded with preferably autologous surface cells 4 which adhere to this surface and are cells with a chondrogenic potential (e.g., during in vitro proliferation de-differentiated chondrocytes or cells with a stem cell character).

The surface cells 4 adhering to the surface of the implant body 2 adhere advantageously to all surfaces of the implant body and form advantageously one single cell layer, in which the cells are substantially confluent or nearly confluent. However, it is possible also that the surface cells 4 are present in a plurality of superimposed cell layers. If an implant body is produced by in vitro tissue culture and is then trimmed to fit into a specific defect, trimming is carried out preferably immediately before implantation, i.e. after the step of coating, such that the narrow sides 5 of the implant body 2 show no adhering surface cells 4.

Figure 4:
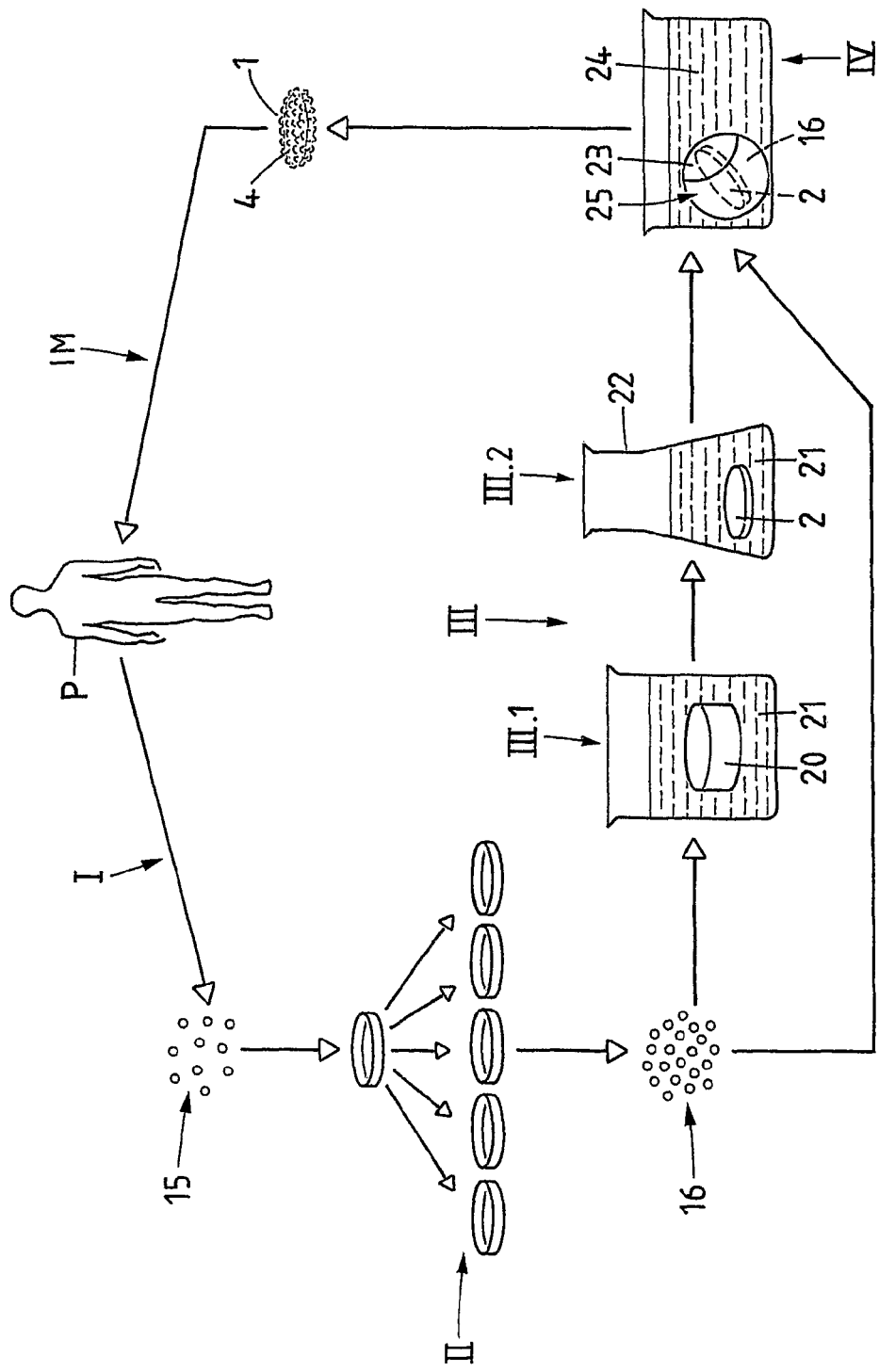
FIGS. 4 to 6 are diagrams representing different embodiments of a method for manufacturing the implant according to the invention.

In another embodiment of the invention, the implant 1 may comprise full thickness channels 6 going through the implant body 2 produced by using a correspondingly shaped space for the step of tissue culturing (see description of FIG. 4). The inner surfaces of the channels 6 may also be populated by surface cells 4. Such channels may serve for increasing the surface of the implant body 2 and/or for enhancing cell migration within the implant.

The implant according to FIG. 1 is e.g. 0.5 to 3 mm thick and has a diameter of 5 to 30 mm or more. The channels 6 have e.g. a diameter of 0.5 to 2 mm.

If an implant according to the invention is not used for the repair of an articular cartilage defect but e.g. for the repair of a meniscus, an ear auricle/helix or a nasal septum the implant body is possibly not disk-shaped but is adapted as well as possible to the individual shape of the defect which is to be repaired.

Figure 2:
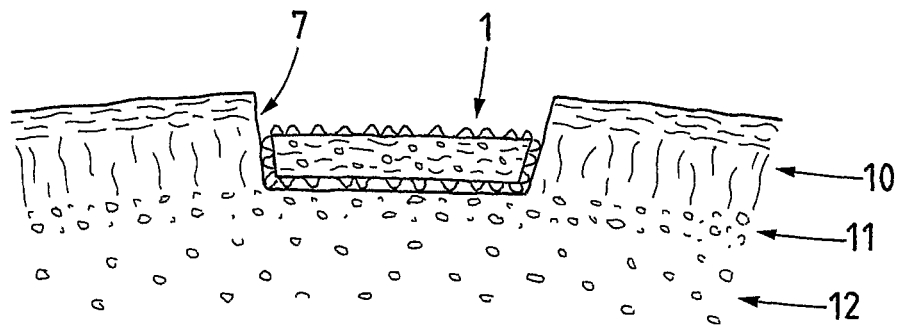
FIGS. 2 and 3 are schematic sections of implants according to alternative embodiments of the invention and being positioned in articular cartilage defects.
Figure 3:
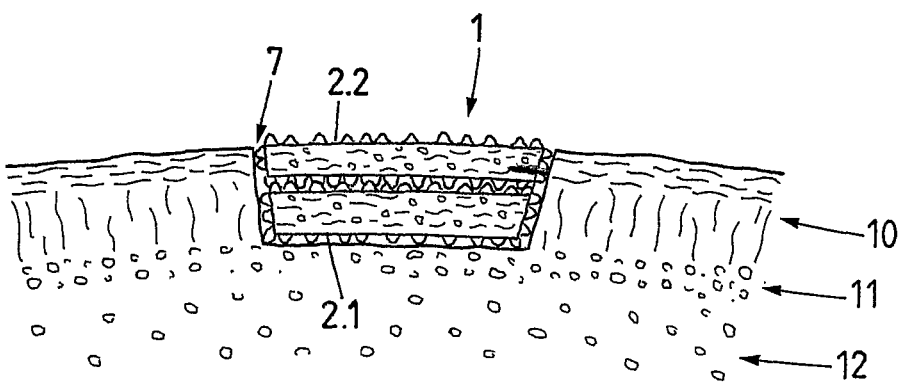

FIGS. 2 and 3 are sections through the implant 1 being positioned in an articular cartilage defect 7. The defect is prepared for the implantation in a per se known manner, by e.g. removing damaged or degenerated cartilage tissue down to the subchondral bone plate 11 separating the natural cartilage layer 10 from the bone tissue 12 underneath. The subchondral bone plate consists of bone material denser than the bone tissue underneath and may be perforated before implantation in a per se known manner. For fixing the implant in the defect a press fit may be sufficient. It is possible also to suture a piece of periosteum over the defect for fixing the implant therein (not shown).

The implant 1 as shown in FIG. 2 corresponds to the implant of FIG. 1. The implant 1 as shown in FIG. 3 comprises two implant body parts 2.1 and 2.2. Autologous surface cells 4 adhere to the surfaces of the implant body parts. For producing the implant as shown in FIG. 3, the implant parts are subjected to a preliminary step of coating being separated from each other and to a final step of coating in a juxtaposed position.

Figure 5:
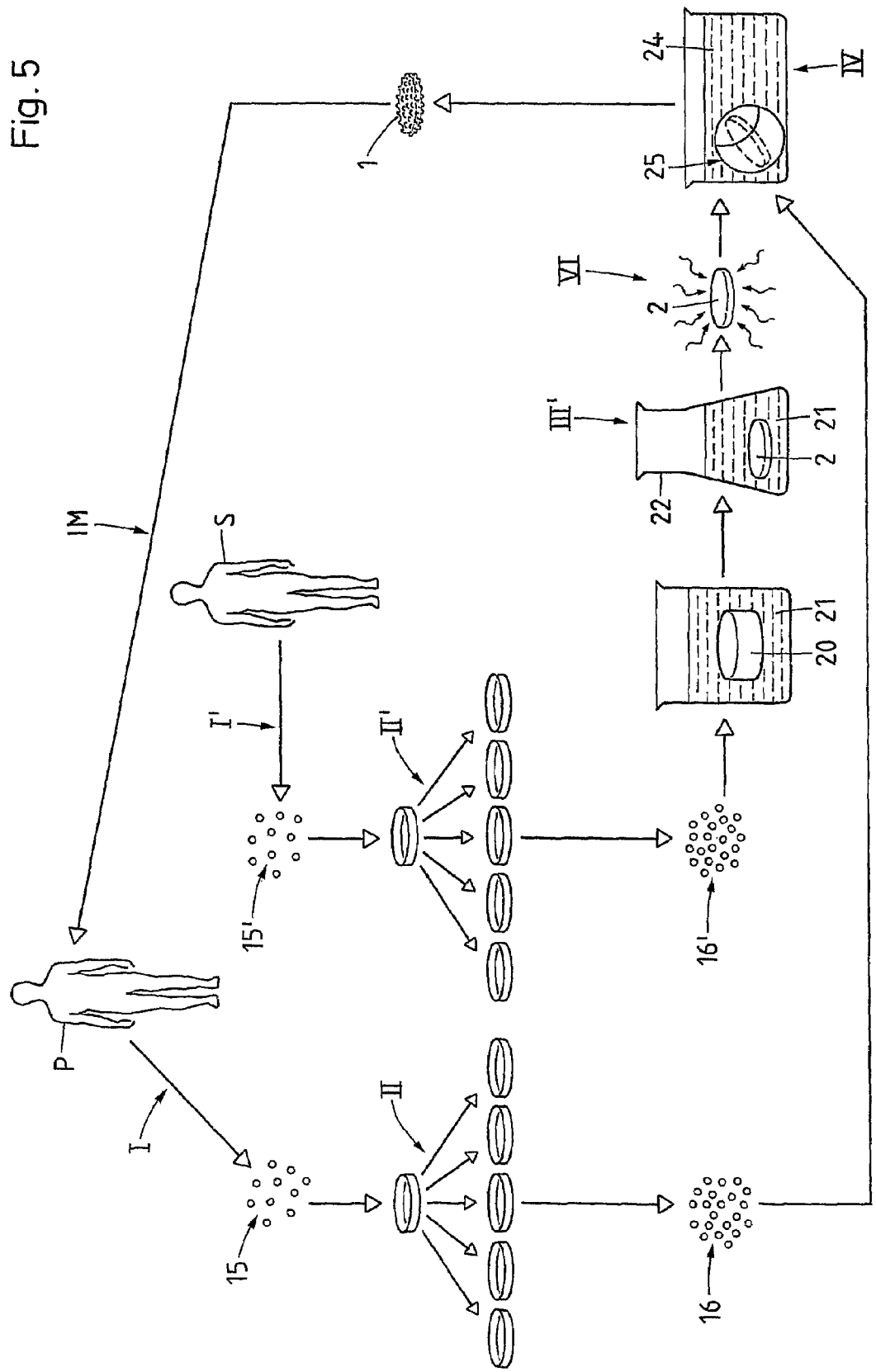
Figure 6:
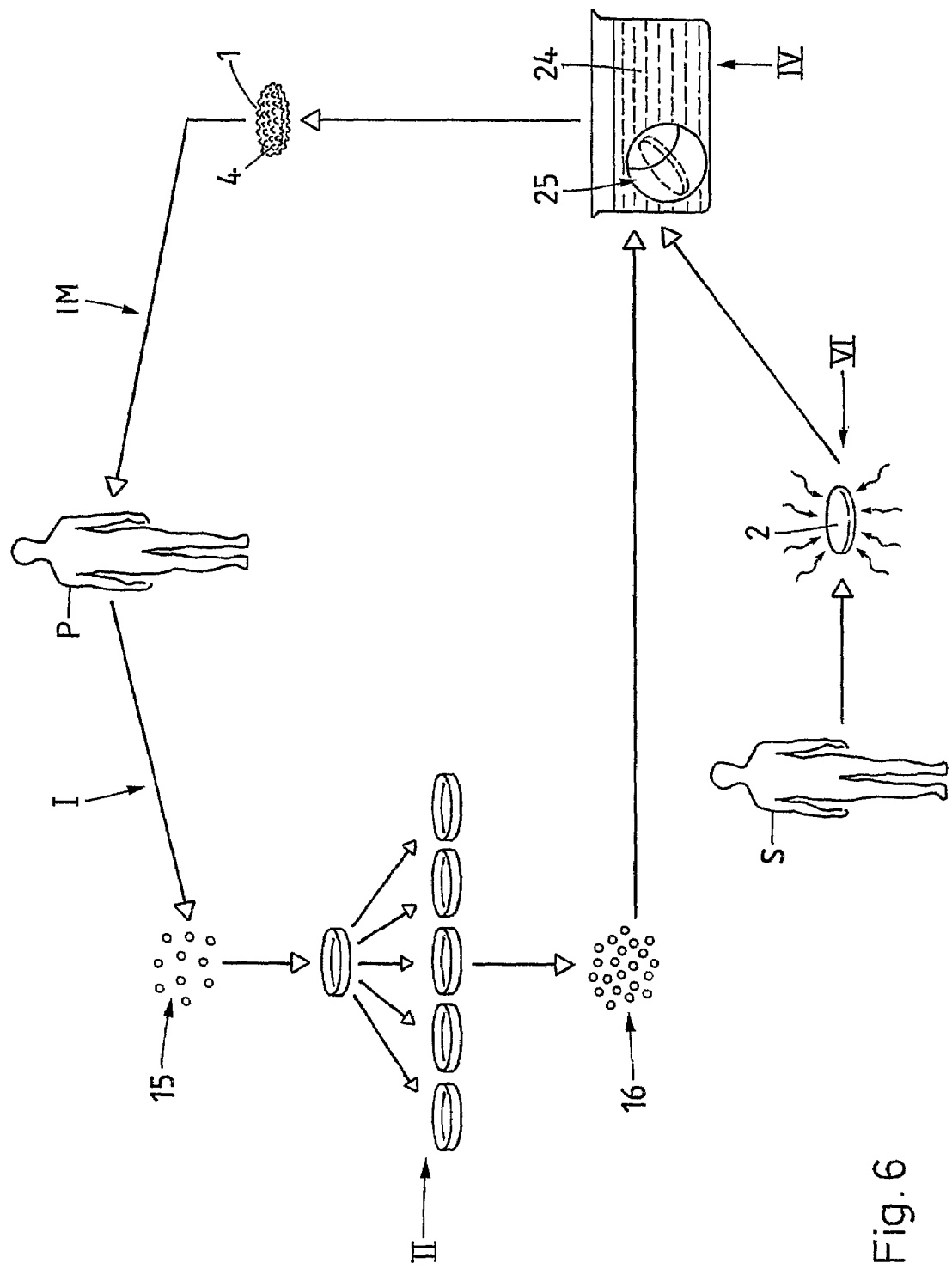

FIGS. 4 to 6 are diagrams illustrating three exemplary embodiments of the method for manufacturing an implant 1 according to various embodiments of the invention. The implant manufactured with a method as illustrated in FIG. 4 consists of viable autologous cartilage tissue produced in vitro. The implant body of an implant manufactured with a method as illustrated in FIG. 5 is a cartilage matrix originating from donor cells, in which matrix the chondrocytes have preferably been destroyed. The implant body of an implant manufactured with a method as illustrated in FIG. 6 consists of a homologous or xenogeneic cartilage matrix from a donor (ex vivo) in which the chondrocytes are destroyed. Following manufacture by any of these methods, the implants may be implanted in the patient P by various methods. In the three Figures same elements are designated with same reference numerals.

FIG. 4 shows a method including the following method steps:

Step I (step of cell procurement): harvesting autologous chondrocytes by excising a cartilage biopsy from a patient P and isolating the autologous chondrocytes 15 from the biopsy;

Step II (step of in vitro cell proliferation): in vitro proliferation of the autologous chondrocytes 15 in a monolayer culture, in which the chondrocytes multiply and thereby are de-differentiated to become de-differentiated chondrocytes;

Step III (step of in vitro tissue culturing): producing an implant body 2 by in vitro three dimensional tissue culturing starting from a first part of the de-differentiated chondrocytes 16 produced in step II; and Step IV (step of implant coating): seeding surfaces of the implant body 2 with autologous surface cells 4 having a chondrogenic potential by culturing the implant body in a suspension containing a second part of the de-differentiated chondrocytes 16 produced in step II.

For steps I, II, III and the implantation IM various per se known methods are applicable. Depending on the number of chondrocytes being isolated from the biopsy, the step of in vitro proliferation may include a plurality of passaging steps. For producing a disk-shaped implant of about 30 mm diameter and being suitable for the repair of an articular cartilage defect about 80,000,000 to 100,000,000 cells are needed for the step of in vitro tissue culturing and about 10,000,000 to 20,000,000 cells for the step of implant coating.

For step II (step of in vitro tissue culturing) the method according to the above mentioned publication WO-97/46665 is the preferred method, wherein preferably two part steps III.1 and III.2 are carried out. In the first part step III.1 a cell suspension is placed in a cell space 20 having semipermeable walls and the cell space is kept without changing its spatial orientation in a suitable culturing medium 21 for about two weeks. In the second part step III.2 the cartilage tissue produced in the cell space 20 is cultured for about another two weeks freely suspended in a suitable culture medium, whereby the tissue grows further and in particular gains mechanical firmness.

The form of the cell space 20 is adapted to the desired implant shape. For producing a disk-shaped implant for the repair of an articular cartilage defect the cell space 20 is flat. If the implant body 2 to be produced is going to have channels 6, as shown in FIG. 1, the cell space 20 is equipped with corresponding columns (not shown) extending through the full height of the cell space. The semipermeable walls of the cell space 20 are permeable for nutrients and so on and they are neither permeable for cells nor for macromolecules being produced by the cells.

The culture medium 21 to be used in the part steps III.1 and III.2 is equipped for enhancing re-differentiation of de-differentiated chondrocytes (e.g., by comprising suitable growth factors).

For step IV (step of implant coating) the surface of the implant body 2 as produced in the step of in vitro tissue culturing (step III) and consisting of autologous cartilage tissue containing viable re-differentiated chondrocytes 3 (FIG. 1) is seeded with de-differentiated chondrocytes 16 as produced in the step of in vitro cell proliferation (step II), wherein the implant body II is positioned in a suspension 23 containing the de-differentiated chondrocytes and its position in the suspension is preferably changed continuously or periodically. With such change it is made sure that the suspended cells 16, which descend by gravity onto the implant body 2 and are supposed to adhere thereon, are uniformly adhered to all surface areas in order to coat the implant body all round. For this purpose the walls of the vessel containing the suspension 23 are made from materials that do not promote and/or inhibit cell adhesion. As time goes by, the condrogenic cells in suspension grow their own individual pericellular matrix and become sticky, promoting cluster formation and at the same time attachment on the implant body 2.

In the step of coating (step IV) 5,000 to 500,000 cells, preferably 10,000 to 100,000 cells are used per $cm^2$ of surface to be seeded, or about 70,000 to 100,000 cells/$cm^2$ which is approximately enough to give one confluent cell layer.

A preferred device for carrying out the step of adhesion culture (step IV) is a hollow body having a form which can be rolled, e.g., a hollow sphere 25. The rollable hollow body is immersed freely rolling in a further culture medium 24, wherein the implant body 2 and the cell suspension 23 of the autologous cells 16 are situated inside the sphere and the sphere comprises a wall which is semipermeable, i.e. permeable for nutrients and additives but non-permeable for cells. The device is shown in more detail in FIG. 7.

If the autologous cells used for seeding the surfaces of the implant body are the same in vitro proliferated autologous chondrocytes 16 as the ones used for the step of in vitro tissue culturing (step III), care has to be taken, that the cells used for the step of coating (step IV) are maintained in about the same state and keep their viability during the approx. four weeks used for the step of in vitro tissue culturing (step III). This is realized by e.g. freezing the cells 16. Of course it is possible also to proliferate the cells 15 isolated from the biopsy in two different cultures, wherein proliferation of the cells used for the step of coating are proliferated more slowly than the cells used for the step of in vitro tissue culturing, which can be achieved e.g. by corresponding choice of culture medium and/or culture temperature. Alternatively, a separate portion of the biopsy harvested from the patient is kept in cell suspension for the amount of time needed and the cell procurement by digestion of this separate part of the biopsy is scheduled in accordance with the progress achieved in generating the cartilage body. Cells intended for coating of the implant body are then ready for use just prior to the implantation date agreed upon with the surgeon.

However, in any embodiment of the invention, it is not required that the autologous cells used in the step of implant coating (step IV) be de-differentiated chondrocytes. Instead other autologous cells having a chondrogenic potential can be used, e.g. stem cells isolated from other tissue.

The step of implant coating (step IV) is based on the fact that chondrocytes or similar cells adhere easily on a cartilage surface, a fact which is e.g. known from the publication by A. C. Chen et al. ("Chondrocyte transplantation to Articular Cartilage Explants in Vitro", J. Orthopaedic Research, 15 (1997), pp. 791-802) and from the publication by R. M. Schinagl et al. ("Effect of Seeding Duration on the Strength of Chondrocyte Adhesion to Articular Cartilage", J. Orthopaedic Research 17 (1999), pp. 121-129). From the publication by M. S. Kurtis et al. ("Integrin-mediated Adhesion of human Articular Chondrocytes to Cartilage", Arthritis & Rheumatisme, 48/1 (2003), pp. 110-118), it is further known that specific integrins play a relevant role in the adhesion of chondrocytes to cartilage surfaces.

For the step of implant coating (step IV) the implant body is cultured in the above described manner for a duration of approximately one to two days.

In embodiments, where the implant body 2 comprises a plurality of implant body parts 2.1 and 2.2 as mentioned in connection with FIG. 3, the implant body parts are subjected to a preliminary step of coating in which the implant body parts are coated separately. The coated implant body parts 2.1 and 2.2 are then positioned against each other and subjected to a final step of coating using a similar cell suspension for another 1 to 2 days. After this final step of coating, the implant body parts are fixed to each other via the surface cells in a manner sufficient for the implant body to be able to be handled as one piece.

FIG. 5 illustrates a further embodiment of the method according to the invention, which method serves for manufacturing the implant 1 which in the present case comprises an implant body 2 which is not grown from autologous cells 16 but from homologous (i.e. allogeneic) or possibly xenogeneic cells 16' having a chondrogenic potential and stemming from a human or animal donor S. For this purpose preferably donor cells are used, which are known to produce little immunogenic reaction (e.g. juvenile chondrocytes, stem cells or genetically modified donor cells). These cells are harvested (step I') and proliferated in vitro (step II'). The implant body 2' which is grown from the cells 16' in a step of in vitro tissue culturing (step III') and contains viable chondrocytes may be subjected, before the step of coating, to an additional step VI, in which the homologous or xenogeneic chondrocytes integrated in the cartilage matrix of the implant body 2 are destroyed. This is e.g. achieved by repeated cycles of freezing and thawing or by exposing the implant body to ultraviolet light after treatment with a suitable die (e.g. methylene blue).

FIG. 6 illustrates a further exemplary embodiment of the method according to the invention which serves for manufacturing an implant 1 suitable for repairing a cartilage defect. In the present case, the implant body stems from a donor S, preferably being a human donor but possibly an animal donor. The implant body therefore consists of ex-vivo cartilage tissue (tissue explant) and is preferably subjected to the additional step VI as described in connection with FIG. 5, in which additional step the homologous or xenogeneic chondrocytes integrated in the cartilage matrix of the implant body are destroyed. The implant body 2 pre-treated in this way is then subjected to the step of implant coating (step IV) in which its surfaces are seeded with autologous cells 16 (e.g., de-differentiated chondrocytes produced in steps I and II). Then the implant is implanted (IM).

Alternatively, the cartilage tissue for the implant body is harvested from the patient P (auto-transplantation), wherein for such an autologous implant body the additional step VI is preferably omitted.

Figure 7:
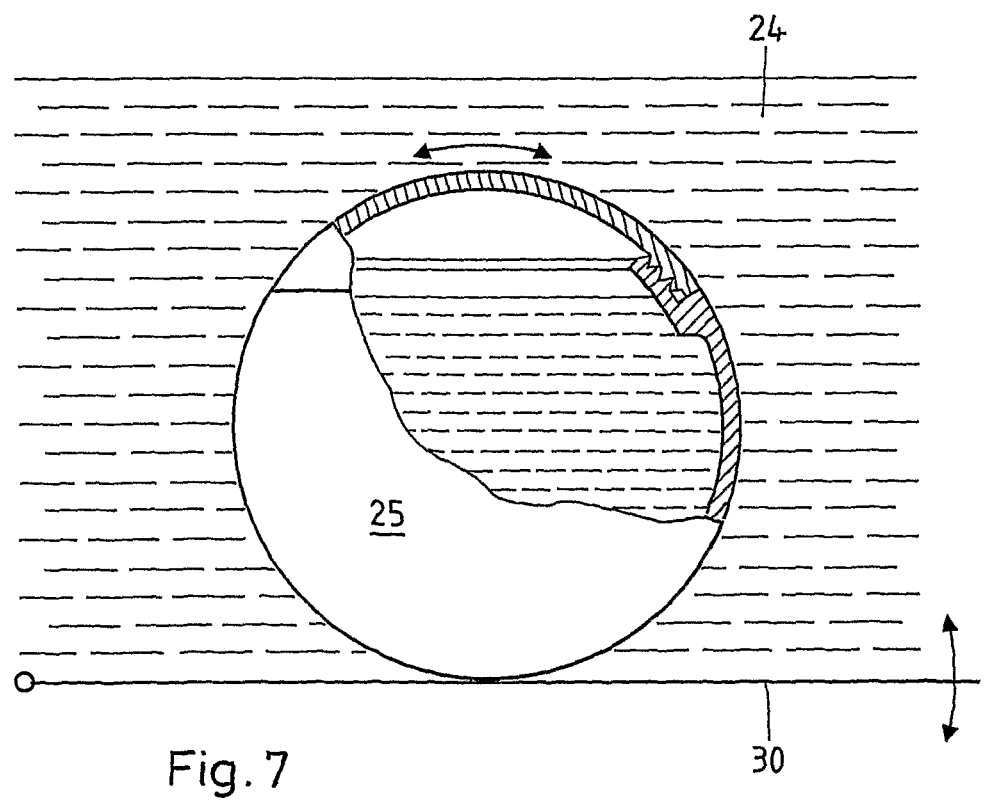
FIG. 7 illustrates in a larger scale a method by which the surface of the implant body is coated with surface cells, e.g., with autologous surface cells.

FIG. 7 shows in a somewhat larger scale a device for carrying out the step of implant coating (step IV), in which the implant body surfaces are seeded with autologous cells and which step is carried out over a period of time sufficient for good adhesion of the cells to the implant body surfaces. As mentioned above, it is preferred to change the spatial orientation of the implant body continuously or periodically during this step such that cells descend on all surfaces of the implant body and adhere to all these surfaces.

The device comprises a hollow roller body, e.g. a hollow sphere 25, which is positioned on the bottom of a container 30. When the container 30 is pivoted, the hollow sphere rolls along its bottom either continuously or periodically. The hollow sphere 25 comprises two parts which are e.g. connected by being snapped or screwed together. The walls of the hollow sphere are semipermeable in a manner as described further above.

The implant body and the cell suspension are brought into the hollow sphere, which is then closed, positioned on the bottom of the container 30 and flooded with culture medium 24. Due to the rolling motion of the hollow sphere 25 gravity acts in changing directions on the implant body such that cells descend on all surfaces of the implant body to adhere thereon. In this way it becomes possible to seed all surfaces of an implant body with cells.

The invention claimed is:

1. An implant comprising:
an implant body comprising a natural cartilage matrix wherein:
chondrocytes that originally produced the matrix are present in a viable or non viable state, and
the natural cartilage matrix is produced by in vitro tissue culturing from cells or produced from ex vivo cartilage tissue; and
viable cells that have a chondrogenic potential adhered to the surface of the implant body;
wherein the implant body has a thickness of 0.5 to 3 mm and at least one other dimension measuring 5 to 30 mm;
wherein the implant body comprises full thickness channels going through the implant body, wherein the channels comprise inside surfaces and the inside surfaces comprise adhered cells.

2. The implant of claim 1, wherein the at least one other dimension is a diameter.

3. The implant of claim 1, wherein the viable cells adhered to the surface of the implant body are autologous cells.

4. The implant of claim 1, wherein the viable cells adhered to the surface of the implant body form a single cell layer.

5. The implant of claim 1, wherein the cartilage matrix of the implant body is produced by in vitro tissue culturing from autologous cells or from autologous ex vivo cartilage tissue and comprises viable chondrocytes.

6. The implant of claim 1, wherein the cartilage matrix of the implant body is produced by in vitro tissue culturing from homologous or xenogeneic donor cells or from ex vivo cartilage tissue from a donor and comprises non-viable chondrocytes.

7. The implant of claim 1, wherein the implant body is disk shaped and wherein at least two opposite disk surfaces comprise adhered cells.

8. The implant of claim 1, wherein the matrix comprises collagen and proteoglycans.

9. The implant of claim 1, wherein the matrix is non-porous.

10. The implant of claim 1, wherein the implant comprises at least two parts.

11. The implant of claim 10 wherein the at least two parts are assembled to form a one piece implant.

12. The implant of claim 1, wherein the viable cells are selected from chondrocytes and stem cells.

13. The implant of claim 12 wherein the chondrocytes comprise de-differentiated chondrocytes that are not re-differentiated.

14. The implant of claim 13 wherein the chondrocytes are de-differentiated in vitro.

15. The implant of claim 12 wherein the chondrocytes comprise juvenile chondrocytes.

16. The implant of claim 3, wherein the single cell layer is not confluent.

17. The implant of claim 1, wherein the viable cells form a plurality of superimposed layers.

18. The implant of claim 1, wherein the implant is adapted to a defect to be repaired.

19. The implant of claim 18 wherein the defect is selected from articular cartilage, meniscus, auricular cartilage and septal cartilage.

20. The implant of claim 17 wherein the defect is the shape of a disk.

21. The implant of claim 17 wherein the implant is sized to be press fit into the defect.

\* \* \* \* \*

UNITED STATES PATENT AND TRADEMARK OFFICE
CERTIFICATE OF CORRECTION

| | | |
|---|---|---|
| PATENT NO. | : 8,945,535 B2 | Page 1 of 3 |
| APPLICATION NO. | : 11/997769 | |
| DATED | : February 3, 2015 | |
| INVENTOR(S) | : Steinwachs et al. | |

It is certified that error appears in the above-identified patent and that said Letters Patent is hereby corrected as shown below:

Title Page, Item (56)

On page 3, in column 1, under "Other Publications", line 1, delete "Chrondrocytes," and insert --Chondrocytes,--, therefor On page 3, in column 1, under "Other Publications", line 19, delete "Trautnatol Arthrosc," and insert --Traumatol Arthrosc,--, therefor On page 3, in column 1, under "Other Publications", line 44, delete "trnasplantation" and insert --transplantation--, therefor On page 4, in column 1, under "Other Publications", line 1, delete "Acutte" and insert --Acute--, therefor On page 4, in column 1, under "Other Publications", line 15, delete Tissue-Engineerd" and insert --Tissue-Engineered--, therefor On page 4, in column 1, under "Other Publications", line 35-36, delete "Mammalizn" and insert --Mammalian--, therefor On page 4, in column 1, under "Other Publications", line 47, delete "Timulates" and insert --Stimulates--, therefor On page 4, in column 2, under "Other Publications", line 1, delete "CArtilage" and insert --Cartilage--, therefor On page 4, in column 2, under "Other Publications", line 32, delete "climical" and insert --clinical--, therefor Signed and Sealed this
Eighteenth Day of August, 2015

Michelle K. Lee
*Director of the United States Patent and Trademark Office*

CERTIFICATE OF CORRECTION (continued)
U.S. Pat. No. 8,945,535 B2

On page 4, in column 2, under "Other Publications", line 45, delete "Comples" and insert --Complex--, therefor On page 4, in column 2, under "Other Publications", line 47, delete "biocompsite" and insert --biocomposite--, therefor On page 4, in column 2, under "Other Publications", line 50, delete "Produciton" and insert --Production--, therefor On page 5, in column 1, under "Other Publications", line 23, delete "TRansfer" and insert --Transfer--, therefor On page 5, in column 1, under "Other Publications", line 29, delete "Artcular" and insert --Articular--, therefor On page 5, in column 2, under "Other Publications", line 22, delete "Sedding" and insert --Seeding--, therefor On page 5, in column 2, under "Other Publications", line 23, delete "Jounral" and insert --Journal--, therefor On page 5, in column 2, under "Other Publications", line 56, delete "mailedOct." and insert --mailed Oct.--, therefor On page 7, in column 1, under "Other Publications", line 23, delete "Preliminaary" and insert --Preliminary--, therefor On page 7, in column 2, under "Other Publications", line 15-16, delete "Maxoffacial" and insert --Maxillofacial--, therefor On page 7, in column 2, under "Other Publications", line 21, delete "(lactideco-gilcolode)" and insert --(lactide-co-glycolide)--, therefor On page 7, in column 2, under "Other Publications", line 44, delete "bon" and insert --bone--, therefor In the Drawings Sheet 3 of 5, Fig. 5, reference numeral 2, in step III', delete "2" and insert --2'--, therefor In the Specification In column 1, line 61, delete "97146665" and insert --97/46665--, therefor

CERTIFICATE OF CORRECTION (continued)
U.S. Pat. No. 8,945,535 B2

In column 5, line 9, delete "exciding" and insert --exceeding--, therefor

In column 6, line 8, delete "condrogenic" and insert --chondrogenic--, therefor

In column 6, line 62, delete "Rheumatisme," and insert --Rheumatism,--, therefor In the Claims In column 8, line 29, in Claim 1, after "potential", insert --and that are--, therefor In column 8, line 26, in Claim 1, before "adhered", insert --said--, therefor